(12) United States Patent
Du et al.

(10) Patent No.: US 10,435,737 B2
(45) Date of Patent: Oct. 8, 2019

(54) DROPLET GENERATING APPARATUS, SYSTEM, AND METHOD

(71) Applicant: Institute of Microbiology, Chinese Academy of Sciences, Beijing (CN)

(72) Inventors: Wenbin Du, Beijing (CN); Peng Xu, Beijing (CN); Libing Dong, Beijing (CN)

(73) Assignee: INSTITUTE OF MICROBIOLOGY, CHINESE ACADEMY OF SCIENCES, Beijing (CN)

( * ) Notice: Subject to any disclaimer, the term of this patent is extended or adjusted under 35 U.S.C. 154(b) by 0 days.

(21) Appl. No.: 15/598,201

(22) Filed: May 17, 2017

(65) Prior Publication Data
US 2017/0253915 A1 Sep. 7, 2017

Related U.S. Application Data

(63) Continuation of application No. PCT/CN2015/077621, filed on Apr. 28, 2015.

(30) Foreign Application Priority Data

Nov. 17, 2014 (CN) .......................... 2014 1 0655191
Nov. 17, 2014 (CN) .......................... 2014 1 0655309

(51) Int. Cl.
*B01L 3/02* (2006.01)
*C12Q 1/6806* (2018.01)
(Continued)

(52) U.S. Cl.
CPC .............. *C12Q 1/6806* (2013.01); *B01J 2/06* (2013.01); *B01L 3/021* (2013.01); *B01L 3/0268* (2013.01);
(Continued)

(58) Field of Classification Search
CPC ..... B01L 2400/0433; B01L 2400/0439; B01L 2400/0496; B01L 2400/02; B01L 3/021;
(Continued)

(56) References Cited

U.S. PATENT DOCUMENTS 4,302,166 A 11/1981 Fulwyler et al.
4,864,856 A * 9/1989 Ichikawa ............ G01F 23/2966
73/290 V
(Continued)

FOREIGN PATENT DOCUMENTS

CN 101690879 4/2010
CN 101693177 4/2010
(Continued)

OTHER PUBLICATIONS

International Search Report on corresponding PCT application (PCT/CN2015/077621) from International Searching Authority (CN) dated Aug. 20, 2015.
(Continued)

*Primary Examiner* — Brian R Gordon
(74) *Attorney, Agent, or Firm* — Cantor Colburn LLP

(57) ABSTRACT

A droplet generating apparatus, system, and method are disclosed. Based on a relative vibration between a micro-pipe and a container containing a second liquid, a first liquid flowing out from an outlet end of the micro-pipe can be detached from the micro-pipe by a fluid shear force of the second liquid to form droplets in the second liquid. Multitudinous quantitative and uniform droplets can be generated precisely and accurately in the present disclosure.

14 Claims, 12 Drawing Sheets

Specification includes a Sequence Listing.

(51) Int. Cl.
*B01J 2/06* (2006.01)
*G01N 35/10* (2006.01)
(52) U.S. Cl.
CPC .. *G01N 35/1016* (2013.01); *B01L 2200/0673* (2013.01); *B01L 2300/0838* (2013.01); *B01L 2400/02* (2013.01); *B01L 2400/0433* (2013.01); *B01L 2400/0478* (2013.01); *G01N 2035/1034* (2013.01)
(58) Field of Classification Search
CPC .... B01L 3/0268; B01L 3/0421; B01L 3/0217; B01L 3/0234; G01N 35/1002; G01N 35/1009; G01N 35/1016; G01N 2035/1034
See application file for complete search history.

(56) References Cited

U.S. PATENT DOCUMENTS

| | | | | |
|---|---|---|---|---|
| 4,944,922 | A * | 7/1990 | Hayashi | G01N 35/1009 356/624 |
| 6,367,925 | B1 * | 4/2002 | Chen | B01L 3/0268 347/109 |
| 6,537,817 | B1 * | 3/2003 | Papen | B01L 3/0268 134/22.11 |
| 6,599,755 | B1 * | 7/2003 | Eipel | B01L 3/0268 422/547 |
| 2001/0028854 | A1 * | 10/2001 | Ingenhoven | B01L 3/0268 417/413.1 |
| 2004/0071601 | A1 * | 4/2004 | Larson | B01L 3/0268 422/502 |
| 2004/0089825 | A1 * | 5/2004 | Schwenke | B01L 3/0268 250/573 |
| 2005/0269371 | A1 | 12/2005 | Kuo et al. | |
| 2007/0086922 | A1 * | 4/2007 | Andersson | B01L 3/0268 422/400 |
| 2007/0210677 | A1 * | 9/2007 | Larson | B01L 3/0268 310/338 |
| 2007/0269348 | A1 * | 11/2007 | van den Engh | B01L 3/0268 422/400 |
| 2010/0092973 | A1 | 4/2010 | Davies et al. | |
| 2012/0080544 | A1 * | 4/2012 | Shinoda | B01F 5/0256 239/690 |
| 2013/0037623 | A1 * | 2/2013 | Yamaguchi | B01L 3/0268 239/11 |
| 2015/0050719 | A1 * | 2/2015 | Bammesberger | B01L 3/0268 435/286.5 |
| 2016/0202281 | A1 | 7/2016 | Fang et al. | |
| 2016/0258972 | A1 * | 9/2016 | Zordan | B01L 3/021 |

FOREIGN PATENT DOCUMENTS

| | | |
|---|---|---|
| CN | 101957383 | 1/2011 |
| CN | 102232114 | 11/2011 |
| CN | 102925563 | 2/2013 |
| CN | 103008037 | 4/2013 |
| CN | 103394380 | 11/2013 |
| CN | 103954786 | 7/2014 |
| CN | 104324769 | 2/2015 |
| CN | 104450891 | 3/2015 |
| JP | 2013-202555 | 10/2013 |
| WO | WO03013552 | 2/2003 |

OTHER PUBLICATIONS

Nakahsima T et al., Membrane Emulsification by Microporous Glass, Key Engineering Mater, 1991, 513-516:61-62.
Liu. Y et al., Mixing in a multi-inlet vortex mixter (MIVM) for flash nano-precipition, Chemical Engineering Science, 2008, 63(11):2829-2842.
Teh Sy et al., Droplet microfluidics, Lab on a Chip, 2008, 8(2):198-220.
Rissin, D.M. et al., Single-molecule enzyme-linked immunosorbent assay detects serum proteins at subfemtomolar concentrations, Nature Biotechnology, 2010, 28, 595-599.
Tekin Et al., Inkjet printing as a deposition and patterning tool for polymers and inorganic particles, Soft Matter, 2008, 4 (4):703-713.
Meacham JM et al., Droplet formation and ejection from a micromachined ultrasonic droplet generator: Visualization and scaling, Physics of Fluids, 2005, 17(10):100605.
Ferraro P et al., Dispensing nano-pico droplets and liquid patterning by pyroelectrodynamic shooting, Nature Nanotechnology, 2010, 5:429-435.
Tavana H et al., Nanolitre liquid patterning in aqueous environments for spatially defined reagent delivery to mammalian cells, Nature Materials, 2009, 8(9):736-741.
Development of Contact Printing Arrayer and Related Technologies, Zhen-zhong Jia et al., Robot, vol. 29, No. 2, Mar. 2007, 179-185.
Non-contact Liquid Rationing System Based on Compound Intelligent Control, Yaxin Liu et al., Journal of Mechanical Engineering, vol. 46, No. 20, Oct. 2010, 175-181.
Active PHO5 chromatin encompasses variable numbers of nucleosomes at individual promoters, Walter J Jessen et al., Nature Structural & Molecular Biology, Mar. 2006, vol. 13, No. 3, 256-263.
DNA Y Structure: A Versatile, Multidimensional Single Molecule Assay, James T. Inman et al., Nano Letter, 2014, 14, 6475-6480.
Laser-capture microdissection, Virginia Espina et al., Nature Protocols, vol. 1, No. 2, 2006, 586-603.
Obtaining genomes from uncultivated environmental microorganisms using FACS-based single-cell genomics, Christian Rinke et al., vol. 9, No. 5, 2014, 1038-1048.
Passively Driven Integrated Microfluidic System for Separation of Motile Sperm, Brenda S. Cho et al., Analytical Chemistry, vol. 75, No. 7, 2003, 1671-1675.
Nanoliter Reactors Improve Multiple Displacement Amplification of Genomes from Single Cells, Yann Marcy et al., PLoS Genetics, vol. 3, Issue 9, 2007, 1702-1708.
Integrated nanoliter systems, Jong Wook Hong et al., Nature Biotechnology, 2003, vol. 21, No. 10, 1179-1183.
Microfluidics on liquid handling stations (uF-on-LHS): an industry compatible chip interface between microfluidics and automated liquid handling stations, Ansgar Waldbaur et al., Lab on a Chip, 2013, 13, 2337-2343.
Droplet Microfluidics—A Tool for Single-Cell Analysis, H. N. Joensson et al., Angewandte Chemie, 2012, 51, 12176-12192.
Adding Precise Nanoliter Volume Capabilities to Liquid-Handling Automation for Compound Screening Experimentation, Murthy et al., Journal of Laboratory Automation, 2011, 16, 221-228.
Cross-Interface Emulsification for Generating Size-Tunable Droplets, Peng Xu et al., Analytical Chemistry, 2016, 88, 3171-3177.
Single-cell genome sequencing: current state of the science, Charles Gawad et al., Nature Reviews Genetics, 2016, 17(3), 175-188.
Whole-genome multiple displacement amplification from single cells, Claudia Spits et al., Nature Protocol, vol. 1, No. 4, 2006, 1965-1970.
A Quantitative Comparison of Single-Cell Whole Genome Amplification Methods, de Bourcy et al., Plos One, 2014, vol. 9, Issue 8, e105585.
Droplet Microfluidic Technique: Mirodroplets Formation and Manipulation, Chen et al., Chinese Journal of Analytical Chemistry, vol. 40, No. 8, 2012, 1293-1300.
International Search Report on related PCT application (PCT/CN2015/077630) from International Searching Authority (CN) dated Jul. 23, 2015.

* cited by examiner

DROPLET GENERATING APPARATUS, SYSTEM, AND METHOD

CROSS-REFERENCE TO RELATED APPLICATIONS

This application claims all benefits accruing under 35 U.S.C. § 119 from China Patent Application No. 201410655191.5, filed on Nov. 17, 2014, and China Patent Application No. 201410655309.4, filed on Nov. 17, 2014 in the State Intellectual Property Office of China, the contents of which are hereby incorporated by reference. This application is a continuation under 35 U.S.C. § 120 of international patent application PCT/CN2015/077621 filed on Apr. 28, 2015, the content of which is also hereby incorporated by reference.

FIELD

The present disclosure relates to manipulation of microliquid, especially to droplet generating apparatuses, systems, and methods.

BACKGROUND

Precise and accurate manipulation of nanoliter liquid and microliter liquid is very important to modern engineering science, physical science, chemical science, material science, pharmaceutical science, micromachining technology, and widely used in biochemical analysis, environment monitoring, medicine, clinical detection, drug screening, and nanomaterial synthesis and preparation technology. Generating independent water-in-oil or oil-in-water microdroplets is very important to the microliquid manipulation. Multitudinous micro-reactions and micro-screenings can be realized base on the microdroplets. Multitudinous and uniform microdroplets can be prepared by emulsion polymerization (referring to Bovey F A et al., Emulsion polymerization, New York: Interscience publishers, 1955, 1-22), membrane emulsification (referring to Nakahsima T et al., Membrane Emulsification by microporous glass, Key Engineering Mater, 1991, 513:61-61), and spay emulsification (referring to Liu. Y et al., Mixing in a multi-inlet vortex mixer (MIVM) for flash nano-precipition, Chemical Engineering Science, 2008, 63(11):2892-2842). The above methods are mainly applied in microsphere preparation and drug carrier preparation. However, volumes of the microdroplets cannot be precisely and accurately controlled. Therefore, these methods are not suitable for a microreactor or complicated biochemical reaction which require precise and accurate control of the volumes of the microdroplets.

Droplet generating method based on microfluidics (referring to The S Y et al., Droplet microfluidics, Lab on a Chip, 2008, 8(2):198-220) has been developed rapidly in recent years. A microdroplet can be generated in a microchannel of a microfluidic chip based on an unstable interface between a dispersion phase and a continuous phase when they meet in the microchannel. Through different designs of the microfluidic channel, uniform microdroplets can be generated, merged, reacted, and screened. However, the volumes of the microdroplets are limited by the structure of the microchannel and a surface feature modification of the microchannel. In addition, the microdroplets generated in the microchannels must be transferred to a storage container by specific device and method, which increases a difficulty to locate, extract, and analyze the microdroplets.

A simple method used to generate the microdroplet, comprises ejecting or spraying a liquid into a microwell or spotting a liquid on a substrate by a capillary micro-pipe or capillary, for short. However, when the microdroplet is released from the capillary, it is difficult to precisely control the amount of microdroplets due to a surface tension between the liquids inside and outside the capillary, and an adhesion force between the microdroplet and an orifice of the capillary. To overcome the surface tension, piezoelectric ceramics, thermal expansion, high voltage electronic injection, and ultrasound are used to increase a kinetic energy of the microdroplet. To decrease the adhesion force, the structure of an outlet end of the capillary is modified, and the surface of the capillary is coated or silanized. However, complicated and expensive liquid driving devices are used in these methods, and the volumes of the microdroplets are difficult to control directly or defined.

Analysis technology based on digital single molecules and single cells has been developed in recent years. Uniform microdroplets are ideal carriers of the single molecules and the single cells used in quantitative reaction and analysis. A digital nucleic acid molecule amplification technology (e.g. digital polymerase chain reaction, dPCR) is a representative digital nucleic acid quantitative analysis technology, wherein nucleic acid molecules in a sample solution are distributed to a plurality of micro-reaction systems according to the Poisson distribution, each micro-reaction system substantially comprises either one nucleic acid molecule or no nucleic acid molecule, independent amplified reaction is carried out in each micro-reaction system, and the nucleic acid molecules are quantified by counting a number of positive micro-reaction systems. The digital nucleic acid molecule amplification technology is especially suitable for studying variation in counts of gene sequence, such as copy number variation and point mutation.

Digital enzyme linked immunosorbent assay (Digital ELISA) technology which is similar to the digital nucleic acid quantitative analysis technology is also developed in recent years (referring to Rissin, D. M. et al., Single-molecule enzyme-linked immunosorbent assay detects serum proteins at subfemtomolar concentrations, Nature Biotechnology, 2010, 28, 595-599), wherein microspheres containing immune antibodies are put into a femtoliter microwell array, single target protein molecules are selectively combined with the immune antibodies, the microwell array is imaged by enzyme-linked immunoassay, and the single target protein molecules are quantified by counting a number of microwells whose fluorescence signal is amplified.

Digital single cell analysis is one of the hottest fields in modern biology. The digital single cell analysis is an important method to detect cell heterogeneity which is difficult to be found by conventional method, analyze compositions of cell subset, find low-probability cell mutation, and explore uncultured microorganisms. The single cell is too tiny to be manipulated. The single cell of bacteria, fungus, plants and animals can be enveloped in the microdroplet with a diameter ranging from several tens of microns to several hundreds of microns. The microdroplet can supply a microenvironment for the single cell which is convenient to be manipulated. The extracellular materials secreted by the single cell can be gathered quickly in picoliter or nanoliter microdroplets. In addition, multitudinous single cell cultures, enzymatic activity analysis of the single cell, single cell analysis, genome amplification of the single cell, and transcriptome amplification of the single cell can be realized in the microdroplet.

After a molecule solution or a cell solution is mixed with reactants, the mixture can be distributed into a plurality of microsystems. A single molecule or a single cell can be reacted, grown, and amplified in each microsystem, after which an array detection and a digital analysis can be applied to the plurality of microsystems, which improves reliability and sensitivity of biological detection and clinical diagnosis, and has a wide application prospect.

SUMMARY

A simple and low-cost droplet generating technology based on a micro-pipe is provided, by which a nanoliter liquid or a microliter liquid can be manipulated to generate multitudinous droplets quickly, precisely, and accurately, and the quantity of the liquid can be adjusted and controlled freely.

Uniform droplets with controllable size can be generated, which increases precision and efficiency of microreactions of the droplets, and provides an application basis of the droplets in biology and chemistry.

According to one aspect of the present disclosure, a droplet generating apparatus is disclosed. The droplet generating apparatus comprises a liquid driving unit and a vibrating equipment. The liquid driving unit can comprise a liquid driving device configured to inject a first liquid into a micro-pipe connected with the liquid driving device. The vibrating equipment is configured to form a relative motion between the micro-pipe and a container containing a second liquid at a specific frequency and a vibration amplitude to have the first liquid flowed out from an outlet end of the micro-pipe detached from the micro-pipe to form droplets in the second liquid.

The first liquid attached on the outlet end of the micro-pipe can be detached from the micro-pipe by a fluid shear force of the second liquid.

In one embodiment, the relative motion is that the micro-pipe moves back and forth (e.g., vibrates) along a longitudinal axis thereof with respect to the container, and the outlet end of the micro-pipe can repeatedly go across a liquid surface of the second liquid (which is an interface between the second liquid and air, or an interface between the second liquid and a third liquid), using a surface tension and a fluid shear force generated during the crossing of the liquid surface to overcome a surface force between the first liquid inside and outside the micro-pipe and an adhesion force between the first liquid on the outlet end of the micro-pipe, thereby detaching the first liquid on the outlet end from the micro-pipe smoothly. One droplet of the first liquid is formed per cycle of the relative vibration. In one embodiment, the micro-pipe is disposed vertically, and vibrated vertically by the vibrating equipment, and an opening of the container can be defined on an upper side of the container. In another embodiment, the micro-pipe is disposed horizontally, and vibrated horizontally by the vibrating equipment, and the opening of the container can be defined on a side of the container.

In one embodiment, the micro-pipe can be vibrated along a direction perpendicular to the longitudinal axis thereof with respect to the container, and the outlet end of the micro-pipe can swing under the liquid surface of the second liquid, during which the first liquid attached on the outlet end can be detached from the micro-pipe due to the fluid shear force of the second liquid, with a generation throughput of one droplet or two droplets per cycle. In one embodiment, the micro-pipe is disposed vertically, and vibrated horizontally by the vibrating equipment. Because the outlet end of the micro-pipe is under liquid surface in the second liquid all the way, the first liquid flowing out the micro-pipe from the outlet end does not contact with external environment, thereby avoiding contamination to the droplets.

A vibration frequency of the vibrating equipment can be in a range from about 0.1 Hz to about 5000 Hz, such as from about 1 Hz to about 500 Hz, from about 10 Hz to about 250 Hz, from about 30 Hz to about 200 Hz. In one embodiment, the vibration frequency of the vibrating equipment is 50 Hz. A vibration amplitude of the vibrating equipment can be in a range from about 0.5 mm to about 10 mm, such as from about 1 mm to about 5 mm, and from about 2 mm to about 4 mm.

The vibrating equipment and the liquid driving device are not limited in the present disclosure. The vibrating equipment can be an electromagnetic vibrating equipment, a piezoelectric ceramic vibrating equipment, or an eccentric rotating mass (ERM) vibration. The liquid driving device can be a peristaltic pump, a syringe pump, a pressure pump, a pneumatic pump, and an electroosmotic pump.

The micro-pipe can be vibrated up and down to go across the liquid surface of the second liquid repeatedly. A distance between a farthest position out from the second liquid of the outlet end and the liquid surface of the second liquid can be in a range from about 10% to about 90% of the vibration amplitude, such as from about 50% to about 80% of the vibration amplitude.

The droplet generating apparatus can further comprise a moving and locating device. The moving and locating device is configured to substantially maintain a distance between the farthest position outside the second liquid of the outlet end and the liquid surface of the second liquid unchanged when a position of the liquid surface of the second liquid is changed, thereby substantially maintaining the generating conditions of the droplets unchanged to form uniform droplets.

The moving and locating device can directly or indirectly drive the micro-pipe and/or the container to move in a first direction parallel with a vibration direction of the micro-pipe and/or a second direction perpendicular to the vibration direction of the micro-pipe.

The liquid driving unit can further comprise a connecting tube. The liquid driving device can be connected to the micro-pipe through the connecting tube. One single flow channel can be defined in the connecting tube, or a plurality of flow channels can be defined in the connecting tube. The connecting tube can be an airtight tube defining the plurality of flow channels prepared by micromachining or micropackaging. The connecting tube can be connected to a plurality of micro-pipes. The plurality of flow channels can form a flow channel array. The liquid driving unit can further comprise a plurality of connecting tubes. The plurality of connecting tubes can form a connecting tube array. The connecting tube array or the flow channel array can correspond to an array of wells on a microplate such a 96-well microplate. Each connecting tube or each flow channel can be connected to one micro-pipe independently. The droplets can be generated in the array of wells of the microplate simultaneously. The microplate containing the droplets can be used directly in an analysis device or a detection device.

One end of the connecting tube can be fixed to or detachably connected to the liquid driving device, and the other end of the connecting tube can be connected to the micro-pipe. A connecting port can be defined on the end of the connecting tube and connected to the micro-pipe. The micro-pipe can be connected to the connecting port by a threaded connection, a clamping connection, an interference fit, or a plug connection.

The liquid driving unit can comprise a plurality of liquid driving devices. The plurality of liquid driving devices can be connected to a plurality of micro-pipes. The first liquid can be injected into the plurality of micro-pipes at different flow rates by the plurality of liquid driving devices.

The droplet generating apparatus has simple structure and convenient operation method. Multitudinous quantitative and uniform droplets can be generated precisely and accurately by the droplet generating apparatus, thereby decreasing cost of experiment, analysis and detection based on microliquid. A droplet array can also be formed by the droplet generating apparatus quickly, which can be used for digital reaction and detection based on single molecule or single cell.

According to another aspect of the present disclosure, a droplet generating system is disclosed. The droplet generating system comprises the droplet generating apparatus, the micro-pipe, and the container. The droplet generating apparatus comprises the liquid driving unit and the vibrating equipment. The micro-pipe can be air-tight connected to the liquid driving unit and contain the first liquid. The container containing the second liquid is configured to accept droplets of the first liquid.

The micro-pipe can be detachably connected to the liquid driving device. The micro-pipe can be made of at least one of glass, quartz, plastic, and stainless steel. The micro-pipe can be disposable to avoid contamination. In one embodiment, the micro-pipe is made of stainless steel with a high temperature resistance and a high pressure resistance.

At least one microchannel can be defined in the micro-pipe. The outlet end of the micro-pipe can be tapered or cylindrical. The micro-pipe can be selected from a capillary, a bundle of capillaries, a capillary array, and a microfluidic channel. The capillary can be selected from a single core capillary or a multi-core capillary. An upper end of the capillary can be enlarged to form a liquid storage cavity.

A surface of the outlet end of the micro-pipe can have a low surface energy to detach the droplets more smoothly. The surface of the outlet end of the micro-pipe can be modified, such as silanized, to decrease its surface energy.

The container can be in form of a single container, a one-dimensional array of containers, or two-dimensional array of containers. The one dimensional array of containers or the two dimensional array of containers can correspond to the capillary array. The container can be selected from 24-well microplate, 96-well microplate, 384-well microplate, and 1536-well microplate. A bottom of the liquid storage chamber can be flat, tapered, rounded, or oval. In one embodiment, the bottom of the container is flat to accept a droplet array.

Any suitable micro-pipe (e.g. capillary) and container (e.g. microplate) can be used in the droplet generating system, thereby decreasing the cost of the droplet generating system. The container containing the droplets can be directly analyzed and detected, thereby decreasing the cost of the analysis, detection, and reaction based on microliquid.

According to yet another aspect of the present disclosure, a droplet generating method is disclosed, comprising: driving a first liquid out from an outlet end of a micro-pipe continuously or intermittently, while forming a relative vibration between the micro-pipe and a container containing a second liquid to detach the first liquid on the outlet end of the micro-pipe from the micro-pipe to form droplets in the second liquid.

The first liquid on the outlet end of the micro-pipe can be detached from the micro-pipe by a fluid shear force of the second liquid.

The micro-pipe can be vibrated along a longitudinal axis thereof with respect to the container, and the outlet end of the micro-pipe can go across a liquid surface of the second liquid repeatedly. In one embodiment, the micro-pipe is disposed vertically, and vibrated vertically by the vibrating equipment. In one embodiment, the micro-pipe is disposed horizontally, and vibrated horizontally by the vibrating equipment.

The micro-pipe can be vibrated along a direction perpendicular to the longitudinal axis thereof with respect to the container, and the outlet end of the micro-pipe can swing under the liquid surface of the second liquid. In one embodiment, the micro-pipe is disposed vertically, and vibrated horizontally by the vibrating equipment.

A vibration frequency can be in a range from about 0.1 Hz to about 5000 Hz, such as from about 1 Hz to about 500 Hz, from about 10 Hz to about 250 Hz, from about 30 Hz to about 200 Hz. In one embodiment, the vibration is 50 Hz. A vibration amplitude can be in a range from about 0.5 mm to about 10 mm, such as from about 1 mm to about 5 mm, and from about 2 mm to about 4 mm. The first liquid can be different from the second liquid. The first liquid and the second liquid can be insoluble with each other. In another embodiment, an interfacial reaction can be carried out by the first liquid and the second liquid.

The droplets of the first liquid in the second liquid can be further formed into micro-capsules or microspheres by a reaction between the first liquid and the second liquid. The first liquid can be an aqueous solution, such as sample solution, or reactant solution. The second liquid can be oil solution, such as petroleum oil (e.g. n-tetradecane), vegetable oil, silicone oil, and perfluorinated alkane. A surfactant can be added to the second liquid to prevent a fusion between the droplets of the first liquid. The surfactant can be at least one of nonionic surfactant, cationic surfactant, anionic surfactant, and ampholytic ionic surfactant, such as Span®40, Span®80, and Span®83. A volume ratio of the surfactant to the second liquid can in a range from about 0.01% to about 20% (v/v), such as from about 1% to about 10% (v/v).

The materials of the first liquid and the second liquid are not limited and can be varied to meet actual need.

The droplet generating method can further comprise preparing the first liquid, preparing the second liquid, adding the first liquid to the micro-pipe, and adding the second liquid to the container.

A surface of the outlet end of the micro-pipe can be modified, such as silanized, to decrease its surface energy to release the droplets more smoothly.

A third liquid can be covered on the second liquid. The first liquid, the second liquid, and the third liquid can be insoluble with each other. The third liquid can form a sealing layer or a protecting layer on the liquid surface of the second liquid to prevent the second liquid from evaporation or contamination.

In the droplet generating method, an interfacial energy and a fluid shear force at the gas-liquid interface or the liquid-liquid interface can be used to overcome a surface tension and adhesion force of the liquid at the outlet end of the micro-pipe when the outlet end of the micro-pipe having the micro-droplet of the first liquid attached thereon goes across the liquid surface of the second liquid to detach the micro-droplet from the outlet end of the micro-pipe smoothly. Or a fluid shear force can be generated when the outlet end of the micro-pipe having the micro-droplet of the first liquid attached thereon swings in the second liquid to overcome the surface tension and adhesion force of the liquid at the outlet end of the micro-pipe to detach the micro-droplet from the outlet end of the micro-pipe smoothly.

Sizes of the droplets can be controlled by regulating the first liquid. Multitudinous droplets can be generated quickly, precisely, and accurately. In addition, the droplets with controllable sizes and volumes can be directly generated in the second liquid, thereby eliminating a contamination and evaporation of the droplets, and simplifying an extraction and storage of the droplets.

Volumes of the droplets can be controlled by regulating the flow rate of the first liquid, the vibration frequency, the vibration amplitude, etc. The droplets with different components and volumes can be successively generated by changing components of the first liquid, by which not only multitudinous high-throughput screening of the micro-liquid can be realized, but also ultramicro biochemical reaction and detection with multi-steps can be realized.

According to yet another aspect of the present disclosure, an analysis apparatus based on single molecule or single cell is disclosed. The analysis apparatus is configured to analyze a single molecule or a single cell in a microsystem, or carry out a reaction by the single molecule or the single cell in the microsystem.

The analysis apparatus can comprise the droplet generating apparatus, a processing device and/or an analysis device.

A single molecule or a single cell can be contained inside a droplet. The droplet containing the single molecule or the single cell can be applied in PCR (polymerase chain reaction) analysis, single molecule enzyme-linked immunosorbent assay, single cell enzyme activity assay, and single cell genomic amplification sequencing.

The first liquid can be a solution containing molecules or cells. The droplet array can be formed by the first liquid in the second liquid by the droplet generating apparatus.

The molecules can be selected from at least one of nucleic acid molecules, protein molecules, peptide molecules, organic compound molecules, and pharmaceutical molecules.

The cells can be selected from at least one of bacterial cells, fungal cells, plant cells, and animal cells.

The processing device can be selected from at least one of PCR device, heating device, cooling device, and temperature control device. In one embodiment, a platform on which the container is placed can be directly heated or cooled by the heating device or the cooling device. In one embodiment, the processing device further comprises a transfer equipment configured to transport the container to the transfer equipment such as the PCR device.

The container can be in form of a single container, a one-dimensional array of containers, or two-dimensional array of containers. A bottom of the container can be planar. In one embodiment, the container is a microplate, and the micro-pipe is a capillary array corresponding to a well array of the microplate.

The analysis device is configured to analyze the single molecule or the single cell contained in the droplet. The analysis device can be selected from at least one of microscope, fluorescence detection device, and ultraviolet-visible detection device. The container containing the droplets can be directly analyzed and detected by the analysis device.

The analysis apparatus is easy to operate and control. Quantitative and uniform droplets can be generated stably, precisely and accurately. The costs of the micro-pipe and container are low, thereby decreasing cost of the analysis apparatus. The analysis apparatus can be applied broadly in microsystems.

BRIEF DESCRIPTION OF THE DRAWINGS

Implementations are described by way of example only with reference to the attached figures.

DETAILED DESCRIPTION

Figure 1:
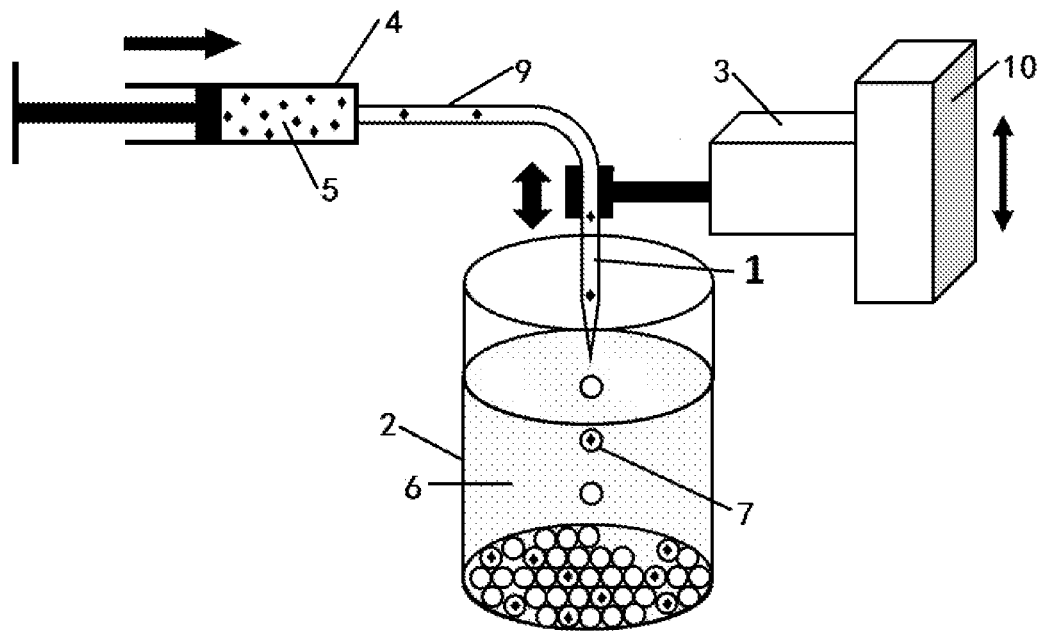
FIG. 1 is a schematic view of one embodiment of a droplet generating apparatus.

A detailed description with the above drawings is made to further illustrate the present disclosure.

A droplet generating apparatus and a droplet generating method are provided in the present disclosure based on a relative movement of a micro-pipe and a container. A first liquid can flow out from an outlet end of the micro-pipe quantitatively. During the relative movement, when the outlet end of the micro-pipe goes across a liquid surface of a second liquid contained in the container, an interfacial energy and a fluid shear force can be generated; or when the outlet end of the micro-pipe swings in the second liquid, the fluid shear force can be generated. Under the action of the interfacial energy and the fluid shear force, the first liquid on the outlet end of the micro-pipe can overcome a surface tension and an adhesive force with an orifice of the outlet end of the micro-pipe, and be released smoothly from the micro-pipe to form a droplet precisely and accurately in the second liquid. Multitudinous droplets (e.g. droplets containing a biochemical sample) can be generated quickly, effectively, and precisely through a continuous flow of the first liquid from the outlet end of the micro-pipe and the high frequency relative movement of the micro-pipe and the container. Furthermore, quantitative droplets with controllable volume and number can be directly produced in a dispersant liquid (the second liquid), thereby eliminating a contamination and evaporation of the droplets, and simplifying an extraction and storage of the droplets.

The first liquid is configured to form the droplets. The second liquid is configured to accept or disperse the droplets. The first liquid can be different from the second liquid. The first liquid and the second liquid can be soluble with, insoluble with or partially soluble with each other. An interfacial reaction can be carried out by the first liquid and the second liquid. The droplets can be liquid droplets formed by the first liquid, or micro-capsules containing the first liquid inside or microspheres formed by the reaction between the first liquid and the second liquid.

The first liquid and the second liquid can be insoluble with each other. In one embodiment, the first liquid can be an aqueous solution, the second liquid can be an oily liquid insoluble with the aqueous solution. The second liquid can be at least one of petroleum oil (e.g. n-tetradecane), vegetable oil, silicone oil, and perfluorinated alkane. The droplets can be formed by the aqueous solution. In one embodiment, the first liquid can be a hydrophobic organic phase, the second liquid can be an oil phase or aqueous phase insoluble with the hydrophobic organic phase. In one embodiment, the first liquid and the second liquid can both be aqueous phase insoluble with each other. For example, the first liquid can be a dextran aqueous solution, and the second liquid can be a polyethylene glycol aqueous solution.

An interfacial reaction can be existed between the first liquid and the second liquid. In one embodiment, the first liquid can be a sodium alginate aqueous solution, the second liquid can be a calcium chloride aqueous solution (e.g. 1% of mass percentage), and the droplets can be calcium alginate gel microspheres.

A third liquid can be covered on the second liquid. The first liquid, the second liquid, and the third liquid can be immiscible with each other. The micro-pipe can be vibrated up and down to go across the liquid-liquid interface between the second liquid and the third liquid repeatedly. In one embodiment, the first liquid can be an aqueous solution, the second liquid can be a perfluorinated oil (e.g. 3M fluorinert FC40), and the third liquid can be a mineral oil. The perfluorinated oil can be covered on the mineral oil due to its lower density. The micro-pipe can be vibrated up and down with respect to an interface between the perfluorinated oil and the mineral oil, and output the first liquid. The droplets formed by the aqueous solution can enter into the perfluorinated oil. The droplets do not sink and can float under a liquid surface of the perfluorinated oil due to its lower density.

Referring to FIG. 1, in one embodiment, the droplet generating apparatus can comprise a liquid driving device 4 (in FIG. 1, a syringe pump) and a vibrating equipment 3. A micro-pipe 1 can be connected to a downstream end of the liquid driving device 4. A first liquid 5 can be filled in a cavity of the syringe pump 4, a connecting tube 9, and the micro-pipe 1. A second liquid 6 can be contained in a container 2 under the micro-pipe 1. The micro-pipe 1 can be vibrated up and down vertically by the vibrating equipment 3. The droplet generating apparatus can further comprise a moving and locating device 10 configured to locate the outlet end of the micro-pipe 1 above the second liquid 6.

The liquid driving device 4 is configured to drive the first liquid 5 in the micro-pipe 1 continuously or intermittently. The liquid driving device 4 can be connected to an end of the micro-pipe 1. The liquid driving device 4 can be selected from a peristaltic pump, a syringe pump, a pressure pump, a pneumatic pump, and an electroosmotic pump. In FIG. 1, the liquid driving device 4 is the syringe pump which is more precise and can drive the first liquid at a flow rate of nanoliters per minute.

The flow rate of the first liquid depends on an inner diameter of the outlet end of the micro-pipe 1, a vibration frequency of the micro-pipe 1, a volume of each droplet, and properties of the first liquid and the second liquid. In the present disclosure, the flow rate of the first liquid can be substantially equal to a product of the vibration frequency of the micro-pipe 1 and a volume of each droplet. In one embodiment, the vibration frequency of the micro-pipe 1 is 50 Hz, the volume of each droplet is 50 picoliter (pL), and the flow rate can be about 50 Hz×50 pL=2.5 nanoliter (nL).

The micro-pipe can have two open ends. One of the two open ends is an inlet end of the micro-pipe 1 and can be connected to the liquid driving device 4, and the other one is the outlet end of the micro-pipe 1. The first liquid can flow into the micro-pipe 1 through the inlet end, and flow out the micro-pipe 1 through the outlet end. The micro-pipe 1 can be selected from a single core capillary, a multi-core capillary, a bundle of capillaries, a capillary array, and a microfluidic channel. In one embodiment, an upper end of the capillary is enlarged to form a liquid storage cavity (similar to a needle of a syringe). In one embodiment, the micro-pipe 1 can be the single core capillary or the capillary array, which is more simple and cost-effective compared with chips used in microfluidics.

The micro-pipe 1 can be disposable. The micro-pipe 1 is usually difficult to wash due to its tiny inner diameter. The disposable micro-pipe 1 can decrease the cost of the droplet generating apparatus. In one embodiment, the micro-pipe 1 can be detachably connected to the liquid driving device 4.

The two open ends of the micro-pipe 1 comprising the inlet and the outlet end can be both cylindrical. The outlet end of the micro-pipe 1 can also be tapered. Sizes of the two open ends, especially a size of the outlet end can be in a range from about 1 μm to about 0.5 mm, such as from about 5 μm to about 0.25 mm. In one embodiment, an inner diameter of the outlet end can be in a range from about 5 μm to about 250 μm, and an outer diameter of the outlet end can be in a range from about 10 μm to 500 μm. To generate smaller droplets, the micro-pipe 1 having a smaller inner diameter is required. In one embodiment, the micro-pipe 1 with an inner diameter of about 100 μm and an outer diameter of about 200 μm is stretched to form a tapered outlet end with an inner diameter of about 30 μm and an outer radius of about 50 μm. The specific structure and size of the micro-pipe 1 are not limited and can be varied to meet actual need.

A surface of the outlet end of the micro-pipe 1 can have a low surface energy to release the droplets 7 more smoothly, thereby increasing the precision of volumes of the droplets 7 and improving uniformity of the droplets 7. The surface of the outlet end of the micro-pipe 1 can be modified to decrease its surface energy. The surface of the outlet end of the micro-pipe 1 can be coated with a low surface coating or silanized.

The liquid driving unit can further comprise a connecting tube 9 configured to transport the first liquid from the liquid driving device 4 to the micro-pipe 1. The liquid driving device 4 can be air-tight connected to the micro-pipe 1 through the connecting tube 9. One end of the connecting tube 9 can be connected to the liquid driving device 4, and the other end of the connecting tube 9 can be connected to the micro-pipe 1. The connecting tube 9 can be made of polytetrafluoroethylene or Teflon®, silicon rubber, polyethylene, or poly vinyl chloride. One single flow channel can be defined in one connecting tube 9, or a plurality of flow channels can be defined in one connecting tube 9. The connecting tube 9 can also comprise a plurality of connecting tubes assembled together. The connecting tube 9 can be an airtight tube defining the plurality of flow channels prepared by micromachining or micropackaging.

The connecting tube 9 can be fixed to or detachably connected to the liquid driving device 4. When the connecting tube 9 contacts the first liquid during droplets generation, the connecting tube 9 can be detachably connected to the liquid driving device 4, so that the connecting tube 9 can be conveniently replaced according to the different type of the first liquid. When the connecting tube 9 cannot contact the first liquid during the droplets generation, the connecting tube 9 can be fixed to the liquid driving device 4 to ensure connection between the connecting tube 9 and the liquid driving device 4 is air-tight.

A connecting port can be defined on the end of the connecting tube 9 connected to the micro-pipe 1. The micro-pipe 1 can be connected with the connecting port by a threaded connection, a clamping connection, an interference fit, or a plug connection. In one embodiment, a structure of the outlet end of the micro-pipe 1 and a structure of the connecting port of the connecting tube 9 are mutually complementary, so that the micro-pipe 1 can be connected to the micro-pipe 1 quickly when replacing the disposable micro-pipe 1. An inner diameter of the connecting tube 9 can be matched with the outer diameter of the micro-pipe 1. The micro-pipe 1 can be directly connected to the connecting port. A connecting joint of the micro-pipe 1 and the connecting tube 9 can be sealed by an adhesive to prevent leakage of the first liquid.

If the micro-pipe 1 is a single core capillary or a multi-core capillary, one connecting tube 9 can be used. If the micro-pipe 1 is the capillary array in which a plurality of capillaries do not contact with each other, the plurality of connecting tubes each defining one flow channel can be used, or one connecting tube defining the plurality of flow channels can be used (referring to FIG. 28 to FIG. 30). The plurality of flow channels can be arranged corresponding to a plurality of containers. In one embodiment, the plurality of flow channels can be arranged corresponding to a pore array of a perforate plate.

The arrangement of the plurality of flow channels can be corresponding to a well array of a microplate in common use such as 96-well microplate, 384-well microplate, and 1536-well microplate, thereby decreasing the cost of the droplet generating apparatus, and increasing universality of the generating apparatus. In addition, the droplet generating apparatus can be used in combination with other detection devices. In one embodiment, the micro-pipe is a chip defining a plurality of microchannels. An inlet opening is defined at one end of the microchannel. An inner diameter of the inlet opening can be in a range from about 0.5 mm to about 2 mm. The connecting tube 9 can be directly inserted into the inlet opening of the chip. An outlet opening can be defined on the other end of the microchannel. The chip can be made of an elastic material (e.g. polydimethyl siloxane). The outer diameter of the connecting tube can be only slightly larger than the inner diameter of the inlet opening, thereby sealing the connecting tube and the inlet opening without the adhesive. When the chip is made of a rigid material such as glass and plastic, a joint between the connecting tube and the inlet opening can be sealed by the adhesive.

Figure 16:
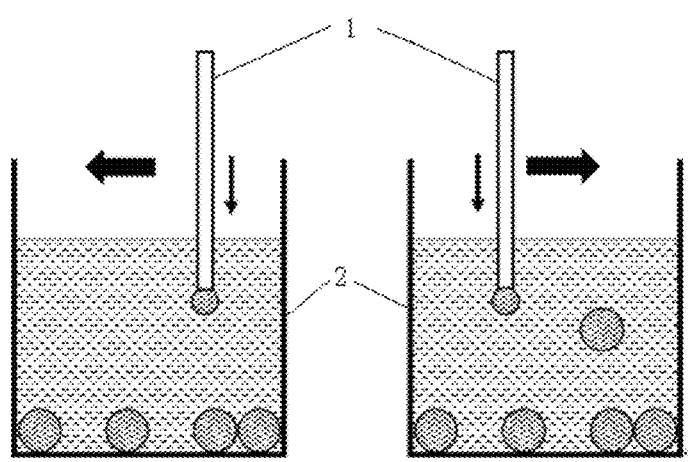
FIG. 16 is a schematic view of a droplet generating process in one cycle in Example 14.

The vibrating equipment 3 is configured to drive the micro-pipe 1 vibrating with respect to the container 2. Referring to FIG. 1, in one embodiment, the vibrating equipment 3 can be connected to the connecting tube 9. The micro-pipe 1 can be driven by the vibrating equipment 3 to a reciprocating vibration with respect to the container 2, during which the outlet end of the micro-pipe 1 goes across the liquid surface of the second liquid repeatedly. Referring to FIG. 16, in another embodiment, the outlet end of the micro-pipe 1 can be driven by the vibrating equipment 3 to a transverse motion under the liquid surface of the second liquid.

The vibrating equipment 3 can drive the reciprocating vibration with a small amplitude and a high vibration frequency. The vibrating equipment 3 can be an electromagnetic vibrating equipment, a piezoelectric ceramic vibrating equipment, or an eccentric rotating mass (ERM) vibration equipment.

The vibration frequency of the vibrating equipment 3 can be fixed, variable, or hierarchical. The vibration frequency of the vibrating equipment 3 can be in a range from about 0.1 Hz to about 5000 Hz, such as from about 1 Hz to about 500 Hz, from about 10 Hz to about 250 Hz, from about 30 Hz to about 200 Hz. In one embodiment, the vibration frequency of the vibrating equipment 3 is 50 Hz.

The amplitude of the vibrating equipment 3 can be adjusted by regulating an input voltage of the vibrating equipment 3. The input voltage of the vibrating equipment 3 can be regulated by an electromagnetic vibrator, a linear motor, an actuating motor, or a stepping motor. The amplitude can be in a range from about 0.5 mm to about 10 mm, such as from about 1 mm to about 5 mm, and from about 2 mm to about 4 mm. If the amplitude is too small, the outlet end of the micro-pipe 1 cannot completely separate from the liquid surface of the second liquid when moving away from the container 2. If the amplitude is too large, the precision of the volumes of the droplets can be decreased. The outlet end of the micro-pipe 1 can reach a highest position and a lowest position during the vibration. The liquid surface of the second liquid can be located between the highest position and the lowest position. In one embodiment, a distance between the highest position and the liquid surface can be in a range from about 5% of the amplitude to about 95% of the amplitude, such as from about 50% of the amplitude to about 80% of the amplitude.

If the container 2 is small, the liquid surface of the second liquid can be elevated while constantly generating the droplets in the second liquid. The droplet generating apparatus can further comprise a moving and locating device 10. The moving and locating device 10 is configured to substantially maintain the distance between the highest position of the outlet end of the micro-pipe 1 and the liquid surface of the second liquid when the position of the liquid surface of the second liquid is changed, thereby substantially maintaining the generating conditions of the plurality of droplets to form uniform droplets. The moving and locating device 10 can be a moving support, which can move in a direction parallel with a vibration direction of the micro-pipe 1. If the micro-pipe 1 is vertically positioned, the moving and locating device 10 can be a vertical lifting support. The moving and locating device 10 can further move in a 2D plane or a 3D space, thereby generating droplets in each container of the containers array one by one.

In one embodiment, the moving and locating device 10 can directly or indirectly drive the micro-pipe 1 to move. Referring to FIG. 1, the moving and locating device 10 can be connected to the vibrating equipment 3, and directly or indirectly drive the micro-pipe 1 to move through the vibrating equipment 3. In another embodiment, the moving and locating device 10 can directly or indirectly drive the container 2 to move. The moving and locating device 10 can drive a support to move, and the container 2 is disposed on the support. Or, the container 2 can be directly disposed on the moving and locating device 10. In another embodiment, the moving and locating device 10 can drive both the micro-pipe 1 and the container 2 to move cooperatively and in coordination.

The moving and locating device 10 can have a function of automatically locating, for example, by detecting a distance to the liquid surface of the second liquid.

The container 2 is configured to contain the second liquid 6, and accept the droplets 7 formed by the first liquid 5. The container 2 can further configured to storage and transfer the droplets 7.

The container 2 can store microliter liquid or nanoliter liquid. The container 2 can store at least one droplet, that is, the container can store a single droplet, or a plurality of droplets. The container 2 can be in form of a single container, a one-dimensional array of containers, or a two-dimensional array of containers. The container 2 can be a microplate, such as a standard 96-well ELISA microplate, a standard 96-well polymerase chain reaction microplate, a 384-well ELISA microplate, or a 384-well polymerase chain reaction microplate. The container array can store multitudinous droplets having specific amount and specific volumes, and the droplets containing specific components. Mixture and reaction of the droplets with the specific components can be taken in the container array. A bottom of the container 2 can be flat, rounded, or tapered.

Referring to FIG. 1, in one embodiment, the micro-pipe 1 can be disposed above the liquid surface of the second liquid. The outlet end of the micro-pipe 1 can face the liquid surface of the second liquid. The distance between the highest position of the outlet end and the liquid surface of the second liquid depends on the amplitude of the vibrating equipment 3.

Figure 2:
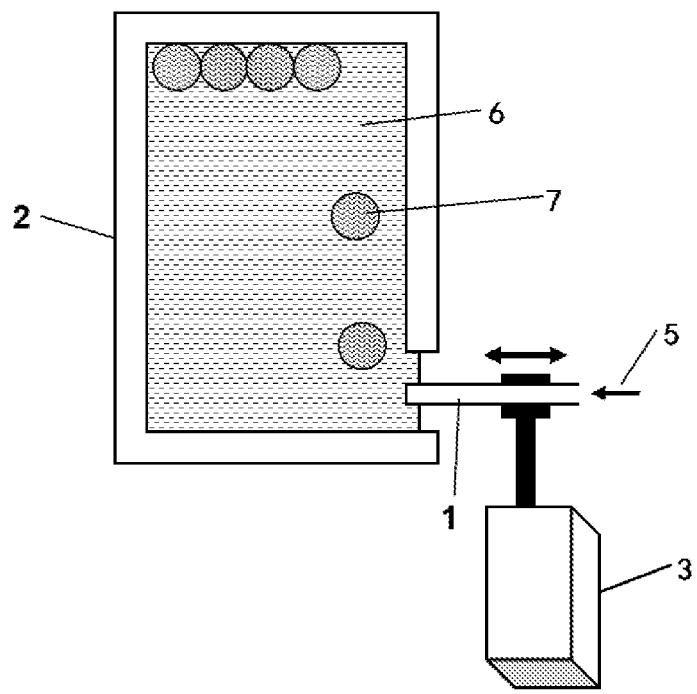
FIG. 2 is a schematic view of another embodiment of the droplet generating apparatus.

Referring to FIG. 2 (wherein the liquid driving device 4 is not shown), in another embodiment, the micro-pipe 1 can be disposed at a side of the container 2. The first liquid 5 can be put into the micro-pipe 1, and the micro-pipe 1 is moved back and forth relative to the second liquid 6 in the container 2 to generate the droplet 7 in the container 2.

It is noted that the relative movement between the micro-pipe 1 and the container 2 essentially refers to a relative movement between the outlet end of the micro-pipe 1 and the container 2. The vibrating equipment 3 can only drive the container 2 to move, the micro-pipe 1 to move, or both the container 2 and the micro-pipe 1 to move cooperatively and in coordination.

Referring to FIG. 1, when the vibrating equipment 3 drives the micro-pipe 1 to move down, the micro-pipe 1 can be moved towards the liquid surface of the second liquid from the highest position until the outlet end or the first liquid on the outlet end enters into the second liquid. When the vibrating equipment 3 drives the micro-pipe 1 to move up, the micro-pipe 1 can be moved away from the second liquid until the outlet end exited out from the second liquid and returns to its original position, during which the first liquid can be released from the outlet end, and kept in and surrounded by the second liquid to form one droplet due to a surface tension and a liquid shear force of the liquid surface of the second liquid.

In one embodiment, the micro-pipe 1 can be vertically disposed, and the outlet end of the micro-pipe 1 can be vibrated up and down with respect to the liquid surface of the second liquid. A distance between the highest position of the outlet end and the liquid surface can be in a range from about 5% of the amplitude to about 95% of the amplitude, such as from about 50% of the amplitude to about 80% of the amplitude, for example, from about 0.5 mm to about 2 mm. In one embodiment, the micro-pipe 1 can be vertically disposed, and the outlet end of the micro-pipe 1 can be vibrated horizontally under the liquid surface of the second liquid. In one embodiment, the micro-pipe 1 can be horizontally disposed, and the outlet end of the micro-pipe 1 can be vibrated horizontally under the liquid surface of the second liquid.

In one embodiment, the vibrating equipment 3 can be connected to the container 2, and directly drive the container 2 to vibrate with respect to the micro-pipe 1. The container 2 can be vibrated up and down, or back and forth by the vibrating equipment 3 to contact the liquid surface of the second liquid with the outlet end of the micro-pipe 1, and to accept the droplets formed by the first liquid.

A plurality of droplets with different components and volumes can be successively generated by changing components of the first liquid, by which not only multitudinous high-throughput screening of the micro-liquid, but also ultramicro biochemical reaction and detection with multi-steps can be realized.

The first liquid can be filled with the micro-pipe 1. The first liquid can be injected into the micro-pipe 1 continuously or intermittently by the liquid driving device 4. In one embodiment, the first liquid can be injected into the micro-pipe 1 continuously in coordinating with the vibration of the outlet end of the micro-pipe 1. In one embodiment, the first liquid can be injected into the micro-pipe 1 at a predetermined flow rate for a predetermine time when the micro-pipe 1 reaches a predetermined position.

Figure 3:
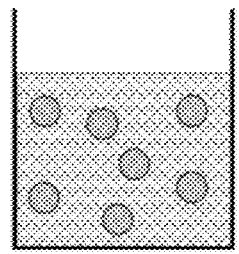
FIG. 3, FIG. 4, and FIG. 5 are graphs respectively showing different embodiments of a droplet distribution in a container.
Figure 4:
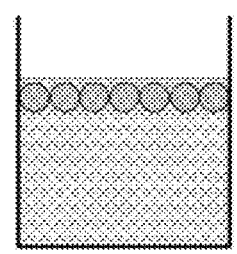
Figure 5:
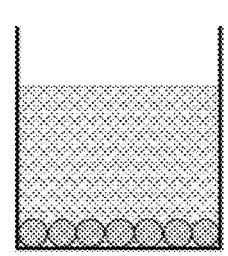

Referring to FIG. 3, when a specific gravity of the first liquid is equal to a specific gravity of the second liquid, the droplets formed by the first liquid can be suspended in the second liquid freely. Referring to FIG. 4, when the specific gravity of the first liquid is smaller than the specific gravity of the second liquid, the droplets can float near the liquid surface of the second liquid to form a droplet array. Referring to FIG. 5, when the specific gravity of the first liquid is larger than the specific gravity of the second liquid, the droplets can sink to a bottom of the container 2 to form a tiled droplet array. By forming the droplet array, location, imaging, detection, extraction, and analysis of the droplets can be more convenient. A contamination of the droplets can be avoided when the droplet array formed at the bottom of the container 2, and signals for analysis and detection of the droplets can be transmitted through the bottom of the container 2.

Diameters and volumes of the droplets can be controlled by regulating the flow rate of the first liquid in the micro-pipe 1, the volume of the first liquid in the micro-pipe 1, the size of the outlet end of the micro-pipe 1, and the vibration frequency and amplitude of the micro-pipe 1. The volumes of the droplets can be controlled in a wide range from about 20 pL to about 10 nL.

In the present disclosure, the micro-pipe 1 can be filled with the first liquid, or at least the outlet end can be filled with the first liquid. The micro-pipe 1 can be disposed above the liquid surface of the second liquid in the container, and then moved towards the liquid surface of the second liquid until contact with and entering into the second liquid. When the first liquid flow out from the outlet end of the micro-pipe 1, the micro-pipe 1 can be moved away from the liquid surface of the second liquid vertically or horizontally until the outlet end is exiting out from the second liquid, during which the first liquid flowing out from the outlet end of the micro-pipe 1 can be separated from the micro-pipe 1, and form one droplet in the second liquid. An interfacial energy and a fluid shear force can be generated when the outlet end of the micro-pipe 1 goes across the liquid surface of the second liquid to overcome a surface tension and an adhesion force between the first liquid and the surface of the outlet end of the micro-pipe 1, so that the first liquid can be released from the micro-pipe 1 smoothly and quantitatively to form the droplets with controllable sizes and volumes. Furthermore, by regulating a vibration frequency of the micro-pipe 1 in which the first liquid is continuously injected into and flowed out, multitudinous droplets (e.g. droplets containing a biochemical sample) with fixed volumes can be generated quickly, effectively, and precisely. As the droplets can be directly generated in a second liquid, an evaporation of the droplets can be avoided, and the extraction and storage of the droplets can be simplified.

An analysis apparatus based on single molecule or single cell comprising the droplet generating apparatus is disclosed. The analysis apparatus can further comprise a processing device and/or an analysis device.

In one embodiment, the processing device can be an amplification device used for single molecule (e.g. nucleic acid molecule) amplification. The amplification device can be selected from a polymerase chain reaction device, a temperature control box, a temperature control heating plate, an infrared heater with a temperature control device, or a wind heater with a temperature control device.

The amplification device and the droplet generating apparatus can be independent from each other, or integrated as one apparatus.

In one embodiment, the amplification device and the droplet generating apparatus are independent from each other, each with their own respective advantages. The droplet generating apparatus can be used as a micro pipette for adding trace amounts of reagents for biological reaction or chemical reaction. The amplification device can be used to carry out an amplified reaction. The container wherein the generated droplets are stored can be transferred to the amplification device. A support for supporting the container during droplet generation can be used to transfer the container and the droplets. The support for supporting the container can be a moving support or a band carrier. The container and the droplets can be transferred to the amplification device smoothly to prevent the fusing of the droplets induced by a vibration of the container.

In another embodiment, the amplification device and the droplet generating apparatus are integrated as one apparatus. After the droplets are generated, the amplified reaction can be carried out directly in the container, thereby avoiding the vibration of the container, and increasing the use convenience of the analysis apparatus.

The amplification device can comprise a temperature controller. The temperature controller is configured to provide a temperature corresponding to each reaction step of the amplified reaction.

The analysis apparatus can further comprise a detection device. The detection device is configured to collect and process signals of the droplets after the amplified reaction, and output detection results.

The detection device can comprise a signal collecting device, a signal processing device, and an output device. The signal collecting device is configured to collect product signals (e.g. fluorescence signals, ultraviolet signals or turbidity signals) after the amplified reaction. The signal processing device can process the product signals according to droplet generating conditions such as the flow rate of the first liquid and the vibration frequency to calculate a quantitative result. The output device is configured to output the detection results.

The signal collecting device, the signal processing device, and the output device is not limited in the present disclosure. The detection device can be an optical microscopic imaging system, a fluorescence scanner, or an integrated imaging sensor. In one embodiment, the detection device is a fluorescence microscopic imaging system, wherein a fluorescence phenomenon of the droplets can be observed, and a number of templates DNA in reaction liquid of the amplified reaction can be obtained by counting fluorogenic droplets. In one embodiment, the droplets can be imaged by the optical microscopic imaging system to obtain all signals of the droplets at one time.

The amplified droplets can further be extracted and used for whole genome sequencing, single nucleotide polymorphism analysis, copy number variation, gene site mutation, and multi-gene expression.

The amplification device and the detection device can be independent from each other, or integrated as one apparatus.

In the analysis apparatus, the first liquid can comprise target molecules or target cells. The first liquid can further comprise reactants for the amplified reaction. The first liquid can be an aqueous solution. In one embodiment, the first liquid can comprise nucleic acid templates, a buffered aqueous solution, deoxyribonucleoside triphosphate (dNTP), a primer, a polymerase, and marking materials of the product of the amplified reaction (e.g. fluorescent material). The first liquid can also be a positive control reaction liquid or a negative control reaction liquid.

The sample to be detected can be micro-quantity of liquid containing a few nucleic acid molecules. The sample can be micro body fluid (e.g. blood), small amount of epidermis, or small amount of mucosa. The sample can comprise a few microorganism (e.g. bacteria, virus, or plasmid) whose quantitative analysis can be realized by detecting specific DNA fragment or RNA fragment of chromosome of the microorganism.

The reaction liquid for the amplified reaction can be nucleic acid amplification reaction liquid (DNA amplification reaction liquid) with deoxyribonucleic acid (DNA) as template, reverse transcription nucleic acid amplification reaction liquid (RNA reverse transcription reaction liquid) with ribonucleic acid as template, or other nucleic acid amplification reaction liquid such as loop-mediated isothermal amplification reaction liquid. The DNA amplification reaction liquid can comprise deoxyribonucleoside triphosphate, buffer solution, inorganic ions, polymerase, primer, and DNA template. The DNA amplification reaction liquid can further comprise marking material for detection such as fluorochrome or fluorescence probe. The RNA reverse transcription reaction liquid can comprise reverse transcriptase, RNA inhibitor, buffer solution, inorganic ions, primer, and RNA template.

The marking material can be fluorochrome or fluorescence probe which can indicate the DNA amplification. The fluorochrome can be combined with DNA, such as SYBR Green. The fluorescence probe can be oligosaccharide probe with fluorophore and quenching group, such as TaqMan fluorescence probe. The marking material can also be nano fluorescent granules, or light absorption material.

The reaction liquid can be pre-mixed uniformly in another container such as a centrifuge tube, and then the marking material can be added to the reaction liquid.

The first liquid can be prepared and diluted before the amplification to ensure that the droplets with predetermined volume comprise at most one molecule to be amplified. That is, each droplet either comprises one molecule to be amplified, or does not comprise any molecule to be amplified. A number ratio of the molecule to be amplified to the droplets can be in a range from about 0.01 to about 0.5, or from about 0.1 to about 0.3.

The first liquid and the second liquid can be insoluble with each other. In one embodiment, the first liquid can be an aqueous solution, and the second liquid can be an oil phase. The second liquid can be a non-volatile liquid with stable chemical property, not react with the first liquid, and have no fluorescence interference. The second liquid can be at least one of mineral oil (e.g. n-tetradecane), vegetable oil, silicon oil, and perfluorinated alkane.

The second liquid can further comprise a surfactant to prevent fusing of the droplets. The surfactant can be inert. A volume ratio of the surfactant to the second liquid can in a range from about 0.01% to about 20% (v/v), such as from about 2% to about 10% (v/v). The surfactant can be at least one of nonionic surfactant, cationic surfactant, anionic surfactant, and ampholytic ionic surfactant, such as Span®40, Span®80, and Span®83. In one embodiment, the surfactant is 5% (v/v) of Span®80.

The second liquid can supply the fluid shear force for the first liquid to form the droplets, and an environment in which the droplets can be preserved stably and isolated from external environment during explicated reaction, thereby avoiding contamination and volatilization of the droplets, and increasing precision of the single molecule analysis apparatus or the single cell analysis apparatus.

In one embodiment, the specific gravity of the first liquid is larger than the specific gravity of the second liquid. The droplets can sink to the bottom of the container and form the droplet array. One layer or a plurality of layers of the droplets can be formed at the bottom of the container. One layer of the droplets is preferred due to detection convenience. In one embodiment, the specific gravity of the first liquid is substantially equal to the specific gravity of the second liquid, the droplets can be dispersed in the second liquid freely. In one embodiment, the specific gravity of the first liquid is smaller to the specific gravity of the second liquid, the droplets can float at an upper portion of the second liquid.

Example 1

Figure 6:
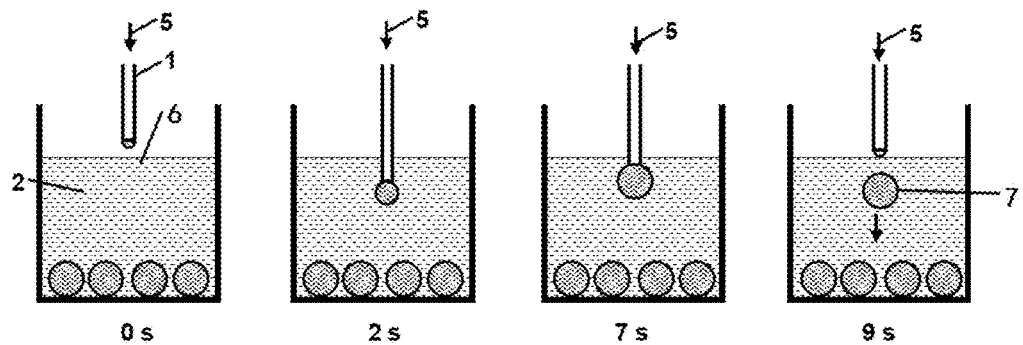
FIG. 6 is a schematic view of one cycle of a droplet generating process in Example 1.
Figure 7:
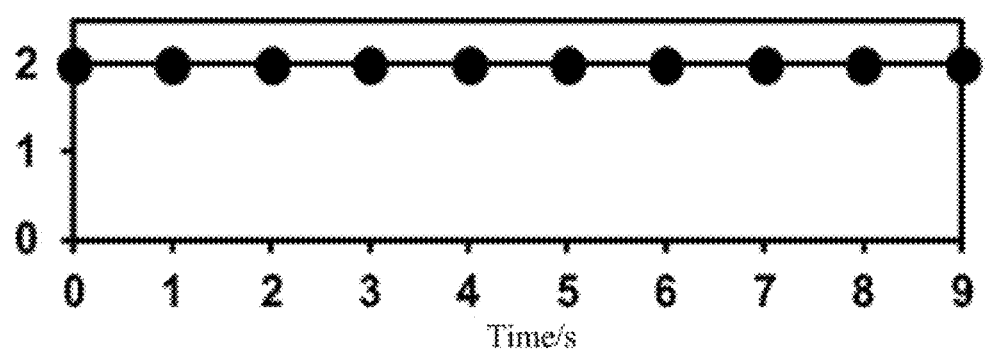
FIG. 7 is a graph showing a flow rate-time curve of water in a capillary in Example 1.
Figure 8:
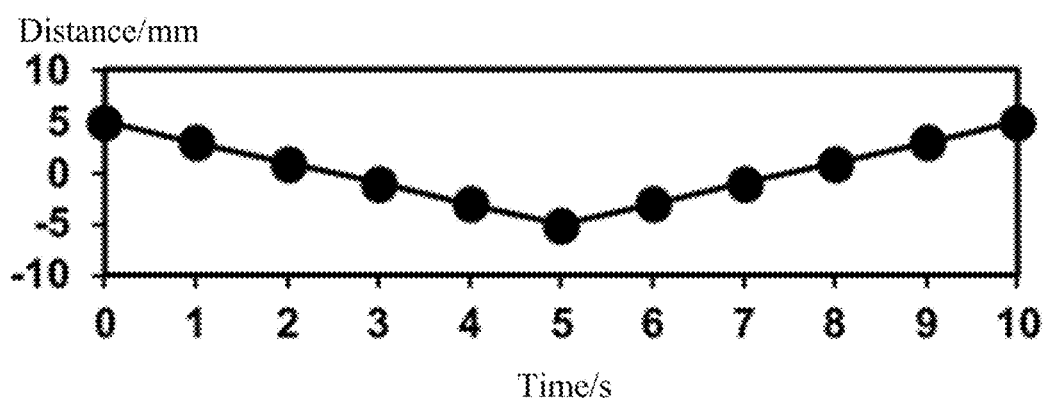
FIG. 8 is a graph showing distance-time curve between an outlet end of the capillary and a liquid surface of a mineral oil in Example 1.

Referring to FIG. 6 to FIG. 8, a quartz capillary 1 is previously silanized by a dichloro dimethyl silane to make its surface hydrophobic. The capillary 1 has an inner diameter of 100 μm, an outer diameter of 300 μm, and a length of 5 cm. An upper end of the capillary 1 is connected to a syringe pump (Harvard Apparatus, Pico Elite, not shown in FIG. 6) through a Teflon® or polytetrafluoroethylene tube with an inner diameter of 300 μm and an outer diameter of 600 μm, wherein connection joints are sealed by an epoxy resin. A syringe (not shown) with a volume of 10 μL is connected to the syringe pump. The syringe, the Teflon® tube, and the capillary 1 are filled with water 5, and a leakage detection is taken before a droplet generating. A glass cell with a length of 1 cm, a width of 1 cm, and a height of 5 cm is used as a container 2. A mineral oil 6 with a volume of 4 mL is put into the container 2.

The capillary 1 is vertically disposed and fixed on a vibrator capable of vibrating up and down. The capillary 1 is vibrated up and down by the vibrator with a vibration frequency of 0.1 Hz and an amplitude of 10 mm. In one cycle (a vibration period of 10 seconds), at zero second, an initial position of an outlet end of the capillary 1 is 5 mm above a liquid surface of the mineral oil 6. The capillary 1 is driven by the vibrator move down vertically at a rate of 2 mm/s from the initial position to enter the mineral oil 6 at a depth of 5 mm. Then the capillary 1 is immediately moved up vertically at a rate of 2 mm/s until it is back to the initial position. During the moving, the water 5 is injected into the capillary 1 continuously at a flow rate of 2 nL/s by the syringe pump, driven out from the outlet end of the capillary 1, and detached from the outlet end of the capillary 1 to form one droplet 7 with a volume of 20 nL in the mineral oil 6 at the 9th second. The droplet 7 sinks to a bottom of the container 2 due to its higher specific gravity. A plurality of uniform droplets each having a volume of 20 nL are generated during the vibration.

The flow rate of the water 5 and the moving speed of the capillary 1 can be increased corresponding to each other to decrease the time for forming the 20 nL droplet.

The injection of the water 5 and the movement of the capillary 1 are continuous, thereby increasing efficiency of generating droplets. Multitudinous droplets can be generated conveniently in this example.

Example 2

The method in Example 2 is substantially the same as the method in Example 1, except that the flow rate of the water injected by the syringe pump is 1 nL/s, 5% (v/v) of Span®80 is pre-added to the mineral oil to prevent fusing of the droplets, and each generated droplet has a volume of 10 nL.

The volume of each droplet can be adjusted by regulating the flow rate of the water.

Example 3

Figures 9, 10:
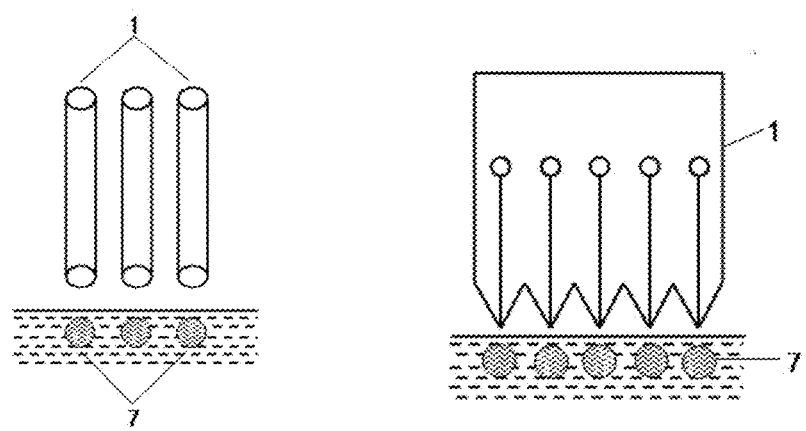
FIG. 9 is a schematic view of one embodiment of a droplet generating method in Example 3.
FIG. 10 is a schematic view of another embodiment of the droplet generating method in Example 4.
Figure 11:
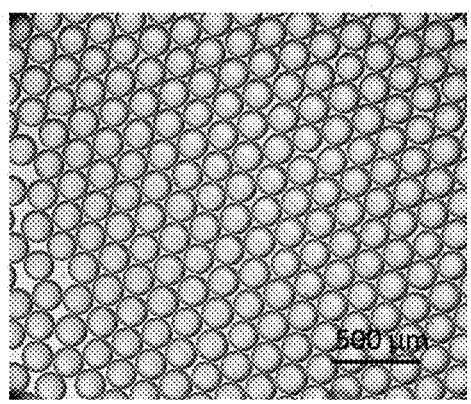
FIG. 11 is a microscope photo of droplets laid on a bottom of a container in Example 5.
Figure 12:
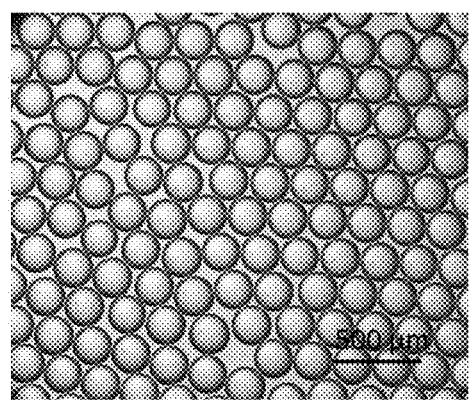
FIG. 12 is a microscope photo of droplets laid on the bottom of a container in Example 6.
Figure 13:
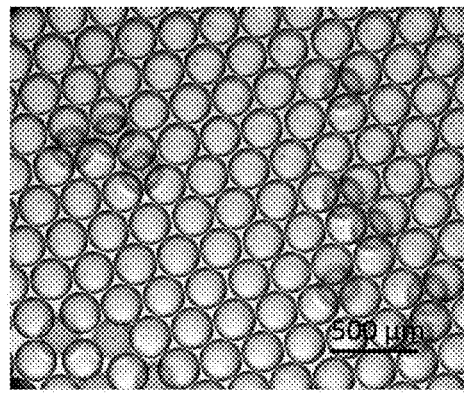
FIG. 13 is a microscope photo of droplets laid on a bottom of a container in Example 7.
Figure 14:
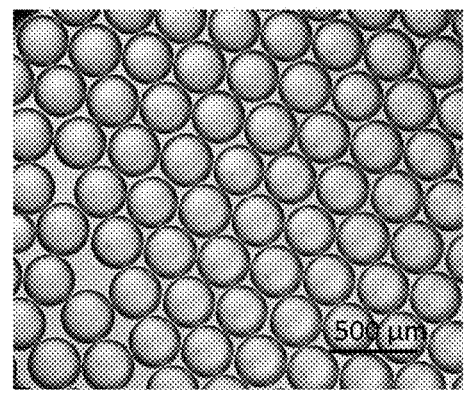
FIG. 14 is a microscope photo of droplets laid on a bottom of a container in Example 8.

Referring to FIG. 9, the method in Example 3 is substantially the same as the method in Example 1, except three parallel capillaries 1 with a space of 2 mm therebetween are used. The three capillaries are respectively connected to three syringes through three silicon rubber tube. Each capillary has an inner diameter of 50 µm and an outer diameter of 155 µm. Each silicon rubber tube has an inner diameter of 150 µm and an outer diameter of 600 µm. A volume of each the syringe is 50 µL. The three syringes are driven by a syringe pump.

Three droplets are generated simultaneously in one cycle. Multitudinous droplets can be generated by using the array of capillaries effectively and conveniently.

Example 4

Referring to FIG. 10, the method in Example 4 is substantially the same as the method in Example 3, except that the three capillaries 1 are replaced by a microfluidic chip 1 defining an array 2-1 of five parallel microchannels 2-2, five inlet 2-3 openings are respectively defined on upper end of the five microchannels, five connecting tubes, made of Teflon are respectively inserted into the five inlet openings, the five tubes are further respectively connected to five syringes with a volume of 50 µL, and the five syringes are driven by a syringe pump having five flow channel.

The microfluidic chip is made of polydimethylsiloxane, and prepared by soft lithography. The microfluidic chip has a thickness of 2 mm, a width of 8.5 mm, and a length of 2 cm. Each microchannel has a depth of 30 µm, a width of 100 µm, and a length of 1 cm. A spacing between adjacent microchannels in the five parallel microchannels is 1.5 mm. Each microchannel corresponds to a tapered outlet end. A diameter of each sample port is 500 µm. Each Teflon® tube has an inner diameter of 300 µm, an outer diameter of 600 µm, and a length of 20 cm. Each Teflon® tubes can be inserted into each inlet openings made by elastic polydimethylsiloxane with a good air tight seal.

Five droplets can be generated simultaneously in one cycle. Multitudinous droplets can be generated by using the array of microchannels effectively and conveniently.

Examples 5 to 8

The methods in Examples 5 to 8 is substantially the same as the method in Example 1, except that the mineral oil 6 is replaced by a tetradecane containing 5% (v/v) of Span®80, the flow rate of the water are respectively 2.4 µL/min, 4.8 µL/min, 6 µL/min, and 12 µL/min, the vibration frequency is 50 Hz, the amplitude of the capillary is 3 mm, the initial position of the outlet end of the capillary 1 is 2 mm above a liquid surface of the tetradecane, and the outlet end of the capillary 1 enters into the tetradecane at a depth of 1 mm when moving down.

Referring to FIG. 11 to FIG. 14, an average diameter of the droplets generated in Example 5 is 178 µm, and a volume standard deviation is 7.2%. An average diameter of the droplets generated in Example 6 is 222.4 µm, an average volume is 5.76 nL, and a volume standard deviation is 6.0%. An average diameter of the droplets generated in Example 7 is 229.3 µm, an average volume is 6.31 nL, and a volume standard deviation is 8.9%. An average diameter of the droplets generated in Example 8 is 305.8 µm, an average volume is 15.0 nL, and a volume standard deviation is 3.0%.

Examples 9 to 13

The methods in Examples 9 to 13 is substantially the same as the method in Example 5, except that the flow rates of the water are respectively 0.06 µL/min, 0.30 µL/min, 0.60 µL/min, 1.2 µL/min, and 18 µL/min.

Figure 15:
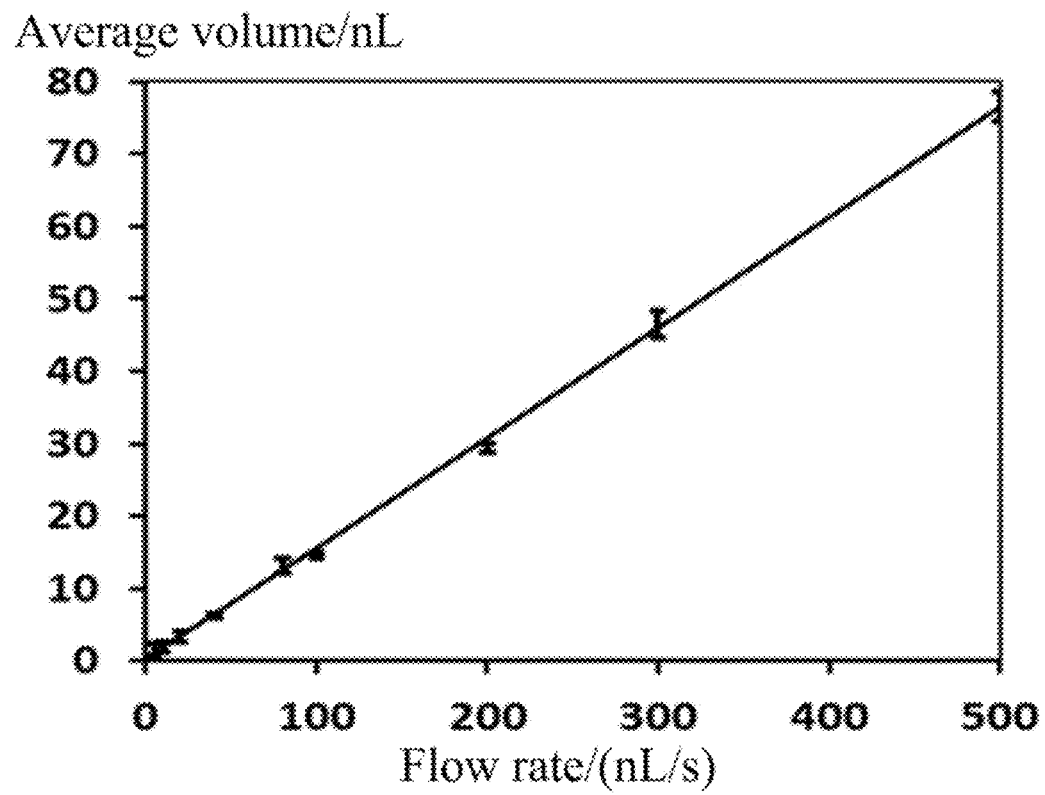
FIG. 15 is a graph showing average volume-flow rate curve of Examples 5 to 13 of the droplets.

Referring to FIG. 15, the average volume of the droplets is calculated according to the average diameter of the droplets. It can be seen from FIG. 15 that there is a significant linear correlation between the flow rate of the water and a volume of the droplet. A formula of the linear fitting is: $v=0.0685 \times f+0.1453$, $R^2=0.9997$, wherein v is the volume of the droplet, and f is the flow rate of the water. It can be concluded that the volume of the droplet can be controlled precisely by regulating the flow rate of the first liquid.

Example 14

Figure 17:
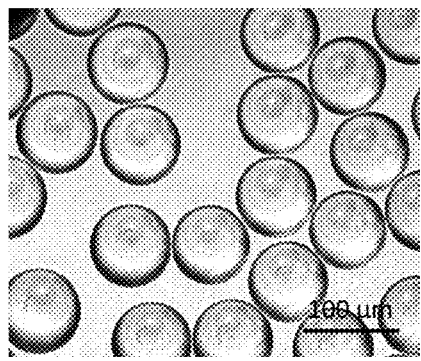
FIG. 17 is a microscope photo of droplets laid on a bottom of a container in Example 14.

Referring to FIG. 16, the micro-pipe 1 is vibrated horizontally under the liquid surface of the first liquid to form the droplets. A capillary 1 with an inner diameter of 25 µm and an outer diameter of 50 µm is connected to a syringe with a volume of 50 µL filled with water by a Teflon® tube. The capillary 1 is inserted vertically under a liquid surface of the mineral oil, and fixed to a vibrating reed of an electromagnetic vibrator. The capillary 1 is vibrated horizontally with a vibration frequency of 50 Hz and an amplitude of 2 mm, during which the outlet end of the capillary 1 is stayed under the liquid surface of the mineral oil. The water is injected to the capillary 1 at a flow rate of 3 µL/min by a syringe pump. Referring to FIG. 17, the average volume of the droplets is 2.63 nL, and a volume standard deviation is 5.5%.

Example 15

Figure 18:
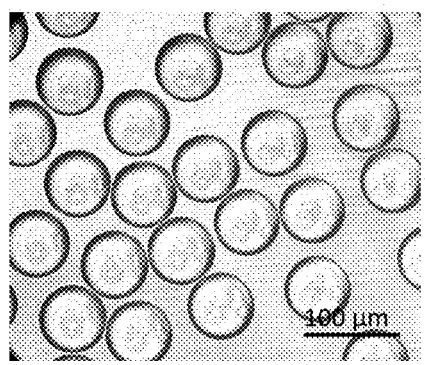
FIG. 18 is a microscope photo of droplets laid on a bottom of a container in Example 15.

The method in Example 15 is substantially the same as the method in Example 14, except that the amplitude is 3 mm. Referring to FIG. 18, the average volume of the droplets is 1.41 nL, and the volume standard deviation is 0.68%.

Example 16

Figure 19:
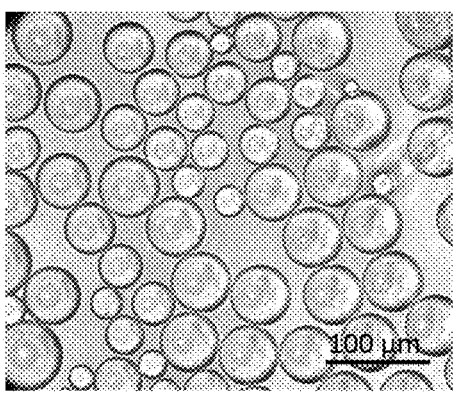
FIG. 19 is a microscope photo of droplets laid on a bottom of a container in Example 16.

The method in Example 16 is substantially the same as the method in Example 14, except that the amplitude is 4 mm. Referring to FIG. 19, the average volume of the droplets is 0.47 nL, and the volume standard deviation is 56.9%.

It can be seen from FIG. 17 to FIG. 19 that sizes and uniformity of the droplets are influenced by the amplitude of the outlet end of the micro-pipe 1 when the outlet end of the micro-pipe 1 is vibrated horizontally in the second liquid with a constant vibration frequency and a constant flow rate of the water. At a flow rate of 3 µL/min of the water, the droplets generated with an amplitude of 2 mm to 3 mm is more uniform than the droplets generated with an amplitude of 4 mm.

The size precision of the droplets is influenced by the flow rate of the first liquid and an amplitude of the outlet end of the micro-pipe 1 when the outlet end of the micro-pipe 1 is vibrated horizontally in the second liquid. The droplets can be directly generated in the second liquid, thereby avoiding contact with air, and eliminating the contamination and the evaporation of the droplets.

Example 17

Sodium alginate microspheres are prepared, and single cell microbe culture is taken in the sodium alginate microspheres in this example.

The first liquid is a sodium alginate aqueous solution containing 0.9% (w/v) of sodium chloride and $1\times10^8$ cell/ml of *Escherichia coli* cells. The second liquid is a 1% (v/v) of calcium chloride aqueous solution.

Figure 20:
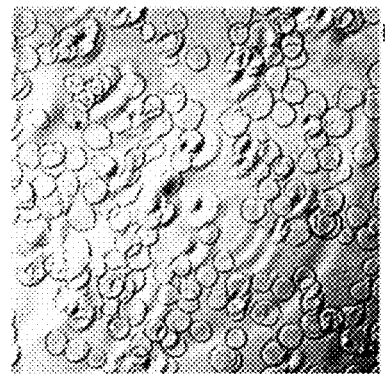
FIG. 20 is a microscope photo of sodium alginate microspheres in Example 17.

A quartz capillary 1 with an inner diameter of 40 µm and an outer diameter of 100 µm is previously silanized by a dichloro dimethyl silane to make its surface hydrophobic. The capillary 1 is vertically fixed on a vibrator and vibrated up and down by the vibrator at a vibration frequency of 50 Hz with an amplitude of 2.5 mm. During vibration, a distance between an outlet end of the capillary 1 and the liquid surface of the second liquid is 2 mm at highest position above the liquid surface, and 0.5 mm at lowest position under the liquid surface. The first liquid is injected into the capillary 1 at a flow rate of 0.3 µL/min to ensure that the capillary 1 is filled with the first liquid. When the first liquid entered into the second liquid along with the outlet end of the capillary 1, the sodium alginate are crosslinked and solidified due to calcium ions to form the sodium alginate microspheres containing *Escherichia coli* cells, and the sodium alginate microspheres are detached from the outlet end of the capillary 1 due to surface tension and fluid shear force. Referring to FIG. 20, a diameter of each sodium alginate microsphere is 32.2 µm with a standard deviation of 8.3%.

After the microspheres are generated, 400 µL of 5% (v/v) of calcium chloride aqueous solution is added to the container to solidify the microspheres again. The microspheres can be separated from the second liquid by centrifugation at 3000 rpm for 3 min, and put into a LB (luria-bertani) culture medium. The *Escherichia coli* cells are cultured at a temperature of 37° C. After the culture, the microspheres are observed by a microscope. A micro-colony grown by the *Escherichia coli* cells is observed. Multitudinous microorganisms can be separated from each other and then be cultured independently by the microspheres. Manipulation, separation, purification, and analysis of the micro-colony are convenient.

Example 18

The method in Example 18 is substantially the same as the method in Example 1, except that the capillary 1 has an inner diameter of 30 µm and an outer diameter of 50 µm. The second liquid is a tetradecane containing 5% (v/v) of Span®80, the first liquid is water.

Comparative Example 1

Figure 22:
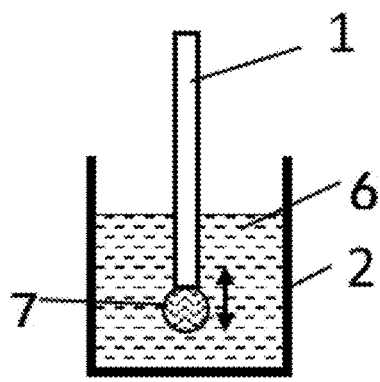
FIG. 22 is a schematic view of a droplet generating method in Comparative Example 1.

Referring to FIG. 22, the method in Comparative Example 1 is substantially the same as the method in Example 18, except that the outlet end of the capillary 1 vibrated up and down under a liquid surface of the tetradecane.

Figure 21:
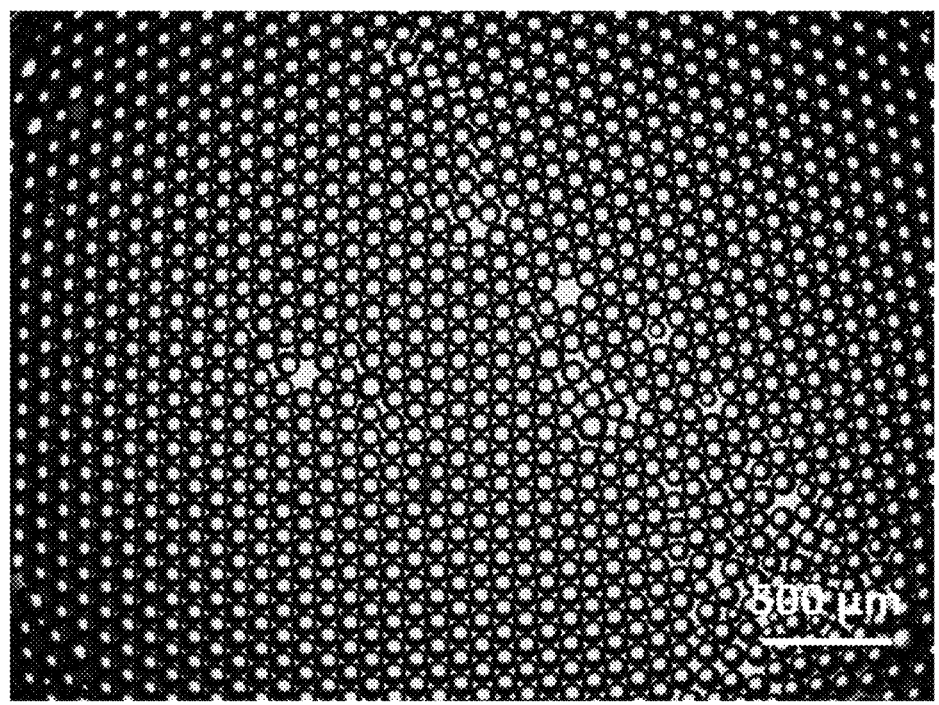
FIG. 21 is a microscope photo of droplets laid on a bottom of a container in Example 18.
Figure 23:
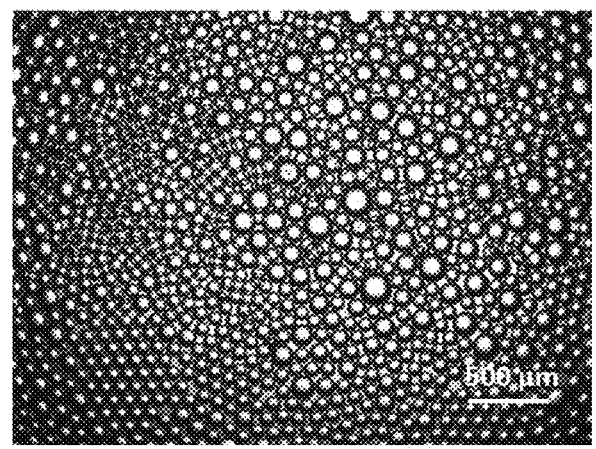
FIG. 23 is a microscope photo of droplets laid on a bottom of a container in Comparative Example 1.

Referring to FIG. 21 and FIG. 23, it can be seen that the droplets generated in Example 18 are more uniform than the droplets generated in Comparative Example 1.

Comparative Example 2

Figure 24:
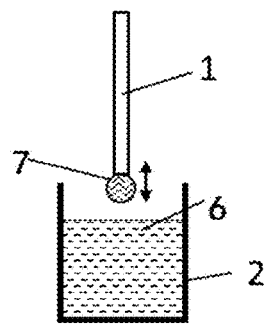
FIG. 24 is a schematic view of a droplet generating method in Comparative Example 2.

Referring to FIG. 24, the method in Comparative Example 1 is substantially the same as the method in Example 18, except that the outlet end of the capillary 1 vibrated up and down above a liquid surface of the tetradecane, and do not contact the liquid surface of the tetradecane.

Figure 25:
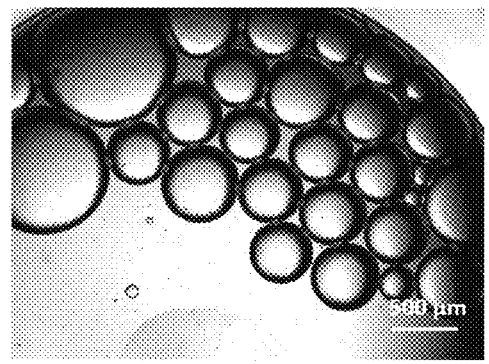
FIG. 25 is a microscope photo of droplets laid on a bottom of a container in Comparative Example 2.

Referring to FIG. 21 and FIG. 25, it can be seen that the droplets generated in Example 18 are more uniform than the droplets generated in Comparative Example 2.

Figure 26:
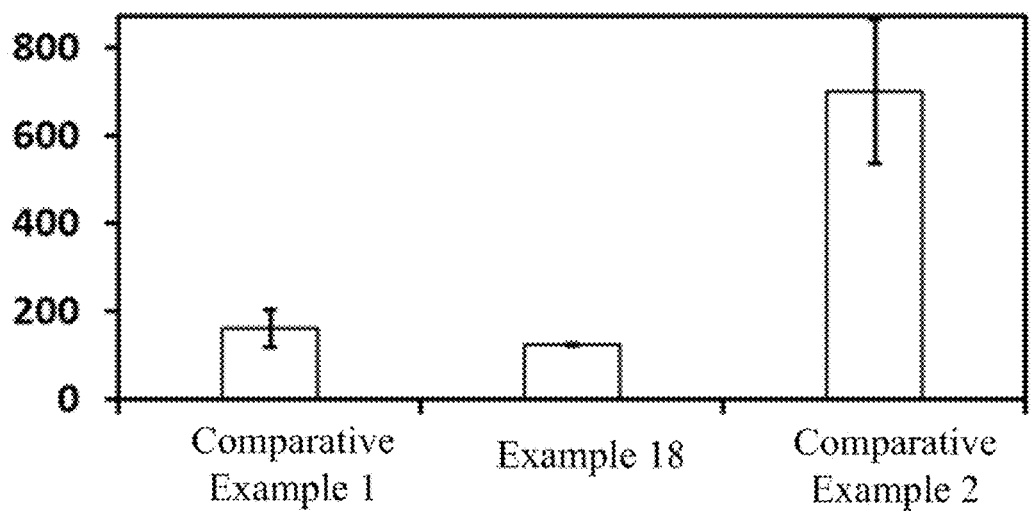
FIG. 26 is a graph comparing average diameter of droplets in Example 18 and Comparative Examples 1 to 2.

Referring to FIG. 26, it can be seen more directly that the droplets generated in Example 18 are more uniform compared to Comparative Examples 1 to 2.

Example 19

Figures 27A, 27B:
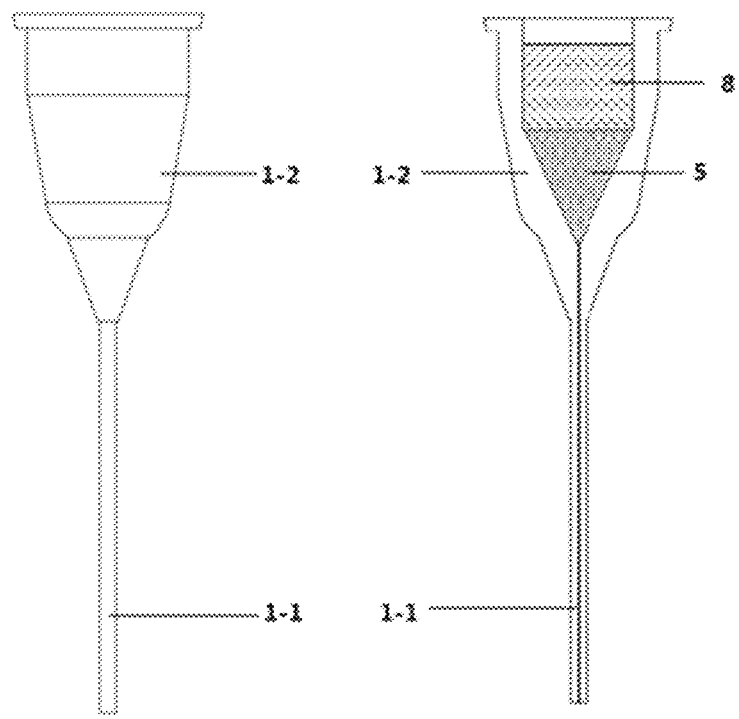
FIG. 27A and FIG. 27B are respectively front view and section view of a micro-pipe in Example 19.

Referring to FIG. 27, a micro-pipe comprising a liquid storage cavity is provided. The micro-pipe can be detachably connected to the connecting tube quickly. The micro-pipe can comprise a straight tube 1-1 and a liquid storage cavity 1-2 defined on an upper end of the straight tube 1-1. The structure of the micro-pipe is similar to a disposable needle of a syringe. The micro-pipe can be made at least one of stainless steel, glass, and quartz. The micro-pipe can be one piece. An inner diameter of the straight tube 1-1 can be in a range from about 50 µm to about 200 µm, such as about 60 µm. An outer diameter of the straight tube 1-1 can be in a range from about 200 µm to about 500 µm, such as about 200 µm. A length of the straight tube 1-1 can be in a range from about 0.5 cm to about 10 cm, such as about 2 cm. The liquid storage cavity 1-2 is configured to store the first liquid 5 containing samples. An mineral oil 8 can be disposed on the first liquid 5 to prevent evaporation of the first liquid. A bottom of the liquid storage cavity 1-2 can be tapered. The upper end of the liquid storage cavity 1-2 is configured to detachably connect to the connecting tube, and can have an inner diameter corresponding to the outer diameter of the connecting tube. An inner diameter of the liquid storage cavity 1-2 can be in a range from about 0.5 mm to about 10 mm, such as about 4 mm. A volume of the liquid storage cavity 1-2 can be in a range from about 10 µL to about 1000 µL, such as about 150 µL.

Example 20

Figure 28:
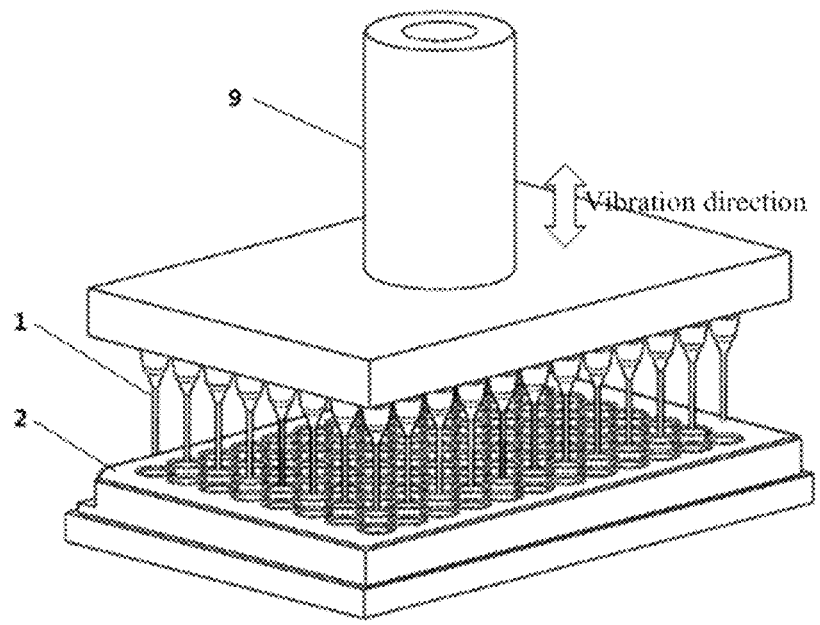
FIG. 28 is a schematic view of a droplet generating system in Example 20.
Figure 29:
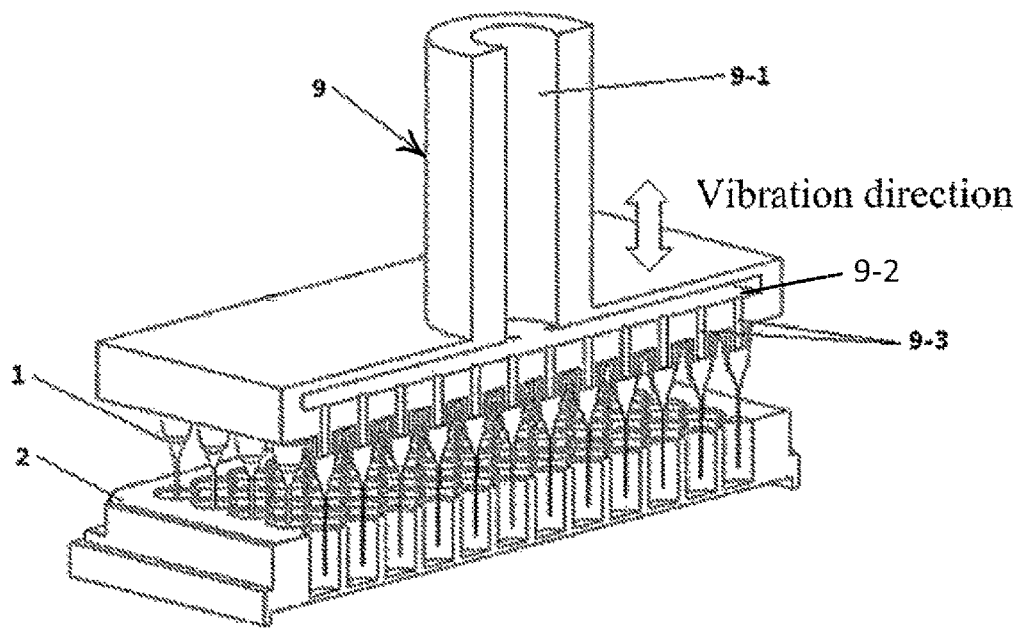
FIG. 29 is a section view of the droplet generating system in Example 20.

Referring to FIG. 28 and FIG. 29, the micro-pipe 1 comprises a plurality of micro-pipes forming a two-dimensional array. Each micro-pipe of Example 20 is the same as the Example 19. The two-dimensional array is formed by ninety-six micro-pipes arranged in nine rows and twelve columns. The connecting tube 9 defines a tubular inlet 9-1, a rectangular cavity 9-2, and a plurality of flow channels 9-3. The tubular inlet 9-1 communicates with the plurality of flow channels 9-3 through the rectangular cavity 9-2. The plurality of flow channels 9-3 are parallel with each other and communicate with the rectangular cavity 9-2 respectively. A bottom end of each flow channel 9-3 is extended to connect with one micro-pipe. The distribution of the plurality of flow channels 9-3 corresponds to the two-dimensional array and a container 2 which is a 96 well microplate. A liquid driving device 4 can connect to the common inlet 2-3 of the array of micro-pipes via a connecting tubing 9. The inner channel 2-4 of the common inlet 2-3 is connected with all flow channels 9-3 above the micro-pipes 1. Each flow channel 9-3 has an inner radius of 4 mm and an outer radius of 6 mm. A spacing of the plurality of flow channels 9-3 is 9 mm The rectangular cavity 9-2 has a length of 12 cm, a width of 8 cm, and a height of 5 mm.

100 μL of a mineral oil is added to each pore of the 96 well microplate. 100 μL of sample liquid is injected into each flow channel firstly. Each micro-pipe is aligned to each pore of the 96 well microplate. A distance between an outlet end of each micro-pipe and the liquid surface of the mineral oil is 2 mm above the liquid surface.

The connecting tube 9 is vibrated by a vibrator at a vibration frequency of 50 Hz and with an amplitude of 3 mm. The flow rate of the sample liquid is 100 nL/s. Fifty droplets each having a volume of 2 nL are generated in each pore in each second. The droplets generating can be repeated only be replacing another 96 well microplate.

The liquid driving device can apply an air pressure on a liquid surface of the sample liquid stored in the liquid storage cavity 1-2 to drive the sample liquid contained in the micro-pipe flow, thereby prevent pollution of the sample liquid to the liquid driving device.

Example 21

Figure 30:
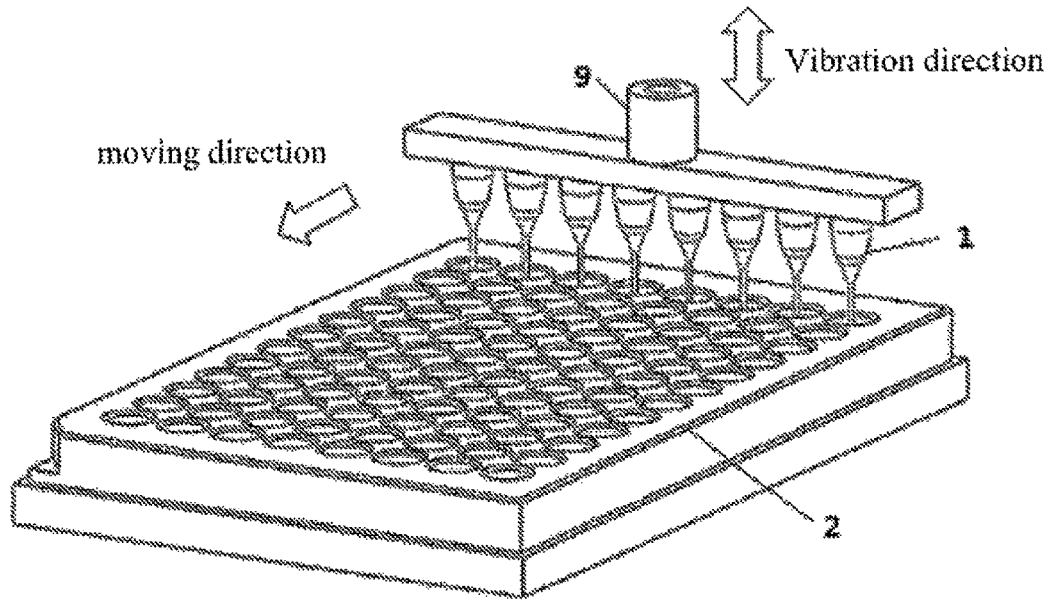
FIG. 30 is a schematic view of the droplet generating system in Example 21.

Referring to FIG. 30, the method in Example 21 is substantially the same as the method in Example 20, except that the micro-pipe is a one-dimensional array formed by eight micro-pipes. Droplets can be generated in one row of pores of the 96 well microplate simultaneously. A liquid driving device 4 can connect to the common inlet 2-3 of the array of micro-pipes via a connecting tubing 9. The one-dimensional array can be moved from one row to another row of pores of the 96 well microplate by the moving and locating device (not shown) to generate droplets in all pores of the 96 well microplate.

Example 22

Figure 31:
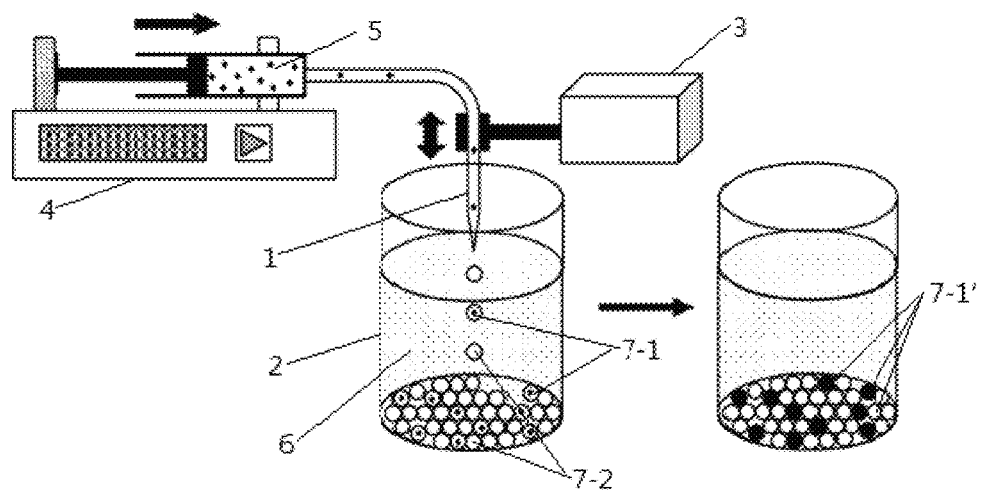
FIG. 31 is a schematic view of an analysis apparatus based on single molecule or singe cell in Example 22.

Referring to FIG. 31, the droplet generating device is used for amplification of singe molecule. The liquid driving device 4 (a syringe pump) is connected to a capillary 1 to form an airtight connection. A first liquid 5 containing a sample is filled with a cavity of the syringe pump and the capillary 1, and flows out an outlet end of the capillary 1 driven by the syringe pump. The capillary 1 is fixed to a vibrating equipment 3 through a clamp, and vibrated up and down along its vertical axis by the vibrating equipment 3. The outlet end of the capillary 1 is vibrated up and down with respect to a liquid surface of the second liquid contained in the container 2. The first liquid and the second liquid are insoluble with each other. When the outlet end of the capillary 1 goes across the liquid surface, the first liquid flowing out from the micro-pipe is released from the outlet end of the micro-pipe to form one droplet. The droplets are arrayed at the bottom of the container 2 due to its larger specific gravity compared with the second liquid. It can be seen from FIG. 31 that some droplets 7-1 each contains one molecule, and some droplets 7-2 each contains none droplet. The container 2 can be put in a nucleic acid amplification device to carry out an amplified reaction. The droplets 7-1' contain amplified nucleic acid molecule.

Example 23

300 ng/μL of λ-DNA (bought from TAKARA corporation, extracted from λ phage) is diluted by a factor of about $10^6$, put into a PCR (Polymerase Chain Reaction) device, and denaturalized at 95° C. for 10 min.

Preparation of LAMP (Loop-mediated isothermal amplification) reaction liquid: supplying 12.5 μL of buffer liquid comprising 40 mmoL/L of Tris-HCl, 20 mmol/L of KCl, 16 mmol/L of $MgSO_4$, 20 mmol/L of $(NH_4)_2SO_4$, 0.2% of Tween®20, 1.6 mol/L of glycine betaine, 2.8 mmol of dNTPs (deoxy-ribonucleoside triphosphate); supplying primers comprising 40 μmol of FIP, 40 μmol of BIP, 20 μmol of Loop-F, 20 μmol of Loop-B, 5 μmol of F3, and 5 μmol of B3; adding the primers, 1 μL of Bst DNA polymerase solution, 1 μL of Calcein, 1 μL of λ-DNA, 2 mg/mL of bovine serum albumin solution, and sterile water to the buffer liquid to form a 25 μL of LAMP reaction liquid.

The gene sequences of the above primer are respectively listed as:

| Primer name | Primer sequence (5'-3') |
|---|---|
| F3 | GAATG CCCGT TCTGC GAG (SEQ ID NO: 1) |
| B3 | TTCAG TTCCT GTGCG TCG (SEQ ID NO: 2) |
| FIP | CAGCA TCCCT TTCGG CATAC CAGGT GGCAA GGGTA ATGAGG (SEQ ID NO: 3) |
| BIP | GGAGG TTGAA GAACT GCGGC AGTCG ATGGC GTTCG TACTC (SEQ ID NO: 4) |
| Loop-F | GGCGG CAGAG TCATA AAGCA (SEQ ID NO: 5) |
| Loop-B | GGCAG ATCTC CAGCC AGGAA CTA (SEQ ID NO: 6) |

150 μL of mineral oil comprising a surfactant is added to a pore of a 96 well microplate with a pore volume of 200 μL and an inner diameter of 8 mm. A capillary with a length of 5 cm, an inner diameter of 30 μm, and an outer diameter of 60 μm is connected to a syringe filled with 50 μL of mineral oil through a Teflon tube with an inner diameter of 300 μm, wherein connection joints are sealed by epoxy resin. The 50 μL of mineral oil contained in the syringe is injected into the Teflon® tube and the capillary by a syringe pump to expel air out the Teflon tube and the capillary.

The LAMP reaction liquid is sucked into the Teflon tube and the capillary by the syringe. The connection joint of the Teflon tube and the capillary is fixed on a vibrating reed of a vibrator. The capillary is hung upon the liquid surface of the mineral oil contained in the pore of the 96 well microplate. A distance between the outlet end of the capillary and the liquid surface is 1 mm. The capillary is vibrated up and down by the vibrator at a vibration frequency of 50 Hz and with an amplitude of 3 mm. The LAMP reaction liquid is injected into the capillary at a flow rate of 100 nL/s with a total volume of 4 μL. After 4 μL of the LAMP reaction liquid is injected, 90% of the bottom of the pore of the 96 well microplate is lie with the generated droplets.

The 96 well microplate is put into the PCR device. The droplets in the 96 well microplate are amplified simultaneously at 63° C. for 1 hours.

Figure 32:
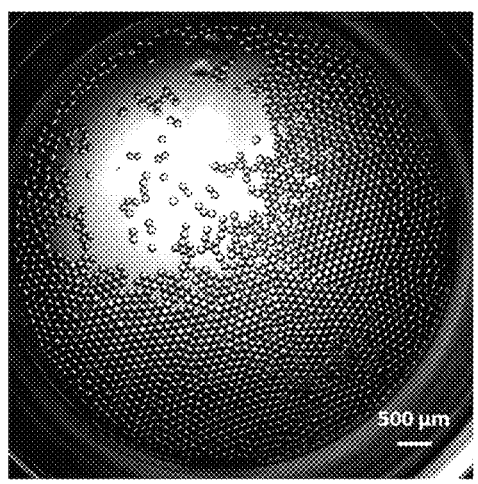
FIG. 32 is a microscope photo of droplets laid on a bottom of a microwell of a 96-well microplate in Example 23.
Figure 33:
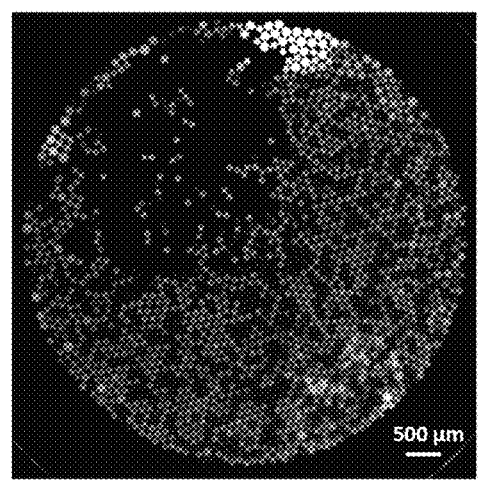
FIG. 33 is a fluorescence microscope of droplets locating in a green fluorescence channel after an amplified reaction in Example 23.
Figure 34:
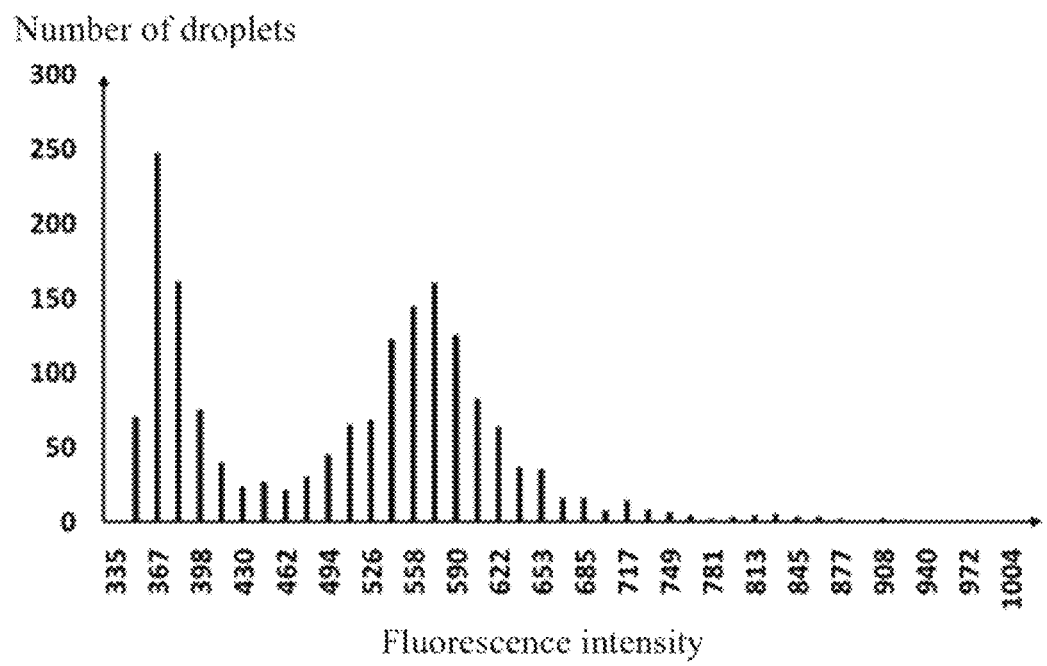
FIG. 34 is a distribution graph of fluorescent droplets after the amplified reaction in Example 23.

Referring to FIG. 32 to FIG. 34, a total number of the generated droplets is 1776. A number of the droplets whose fluorescence intensity is higher than threshold value of 470 is 1105 which is 62% of the total number of the generated droplets, and corresponding to a number of initial DNA templates.

Example 24

The method in Example 24 is substantially the same as the method in Example 23, except that the flow rates of the LAMP reaction liquid are respectively 200 nL/s, 80 nL/s and 10 nL/s to obtain the droplets each having a volume of 4 nL, 1.7 nL, and 0.25 nL.

Figure 35:
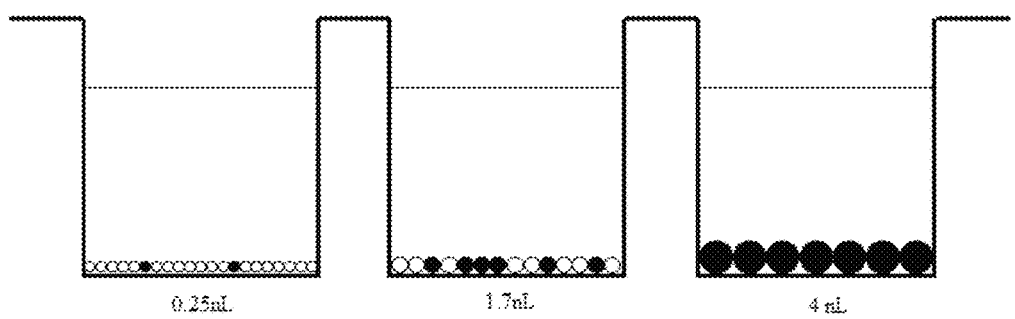
FIG. 35 is a schematic view of droplets with different volumes showing fluorescence in Example 24.

Referring to FIG. 35, it can be seen that the average number of DNA molecule contained in the droplets are decreased along with the average volume of the droplets. The blacked droplet indicates that an amplified reaction are carried out inside.

Finally, it is to be understood that the above embodiments are intended to illustrate rather than limit the present disclosure. Variations may be made to the embodiments without departing from the spirit of the present disclosure as claimed. Elements associated with any of the above embodiments are envisioned to be associated with any other embodiments. The above-described embodiments illustrate the scope of the present disclosure but do not restrict the scope of the present disclosure.

What is claimed is:

1. A droplet generating apparatus comprising:
a micro-pipe having an outlet end, and extending along a longitudinal axis;
a liquid driving device adapted to drive a first liquid through the micro-pipe and out from the outlet end of the micro-pipe;
a connecting tube connected to and extending between the liquid driving device and the micro-pipe;
a vibrating equipment connected to the micro-pipe and adapted to directly vibrate the micro-pipe in an axial direction with respect to the longitudinal axis and transverse to the connecting tube;
a container positioned at least in-part below the micro-pipe; and
a second liquid contained in the container, the vibrating equipment being adapted to operate in coordination with the liquid driving device to dispense the first liquid from the micro-pipe and form a plurality of droplets of the first liquid in the second liquid.

2. The droplet generating apparatus of claim 1, wherein the liquid driving device is configured to drive the first liquid in the micro-pipe out from the outlet end of the micro-pipe at a flow rate in a range from about 2 pL/s to about 50 µL/s.

3. The droplet generating apparatus of claim 1 further comprising:
a moving and locating device connected to the vibrating equipment and adapted to displace the micro-pipe.

4. The droplet generating apparatus of claim 1, wherein the vibration repetitiously displaces the outlet end of the micro-pipe below the liquid surface of the second liquid.

5. The droplet generating apparatus of claim 1, wherein an array of flow channels is defined by the connecting tube.

6. A droplet generating system comprising:
a micro-pipe extending along a longitudinal axis, and having an outlet end;
a container containing a second liquid;
a liquid driving device adapted to drive a first liquid through the micro-pipe and out from the outlet end;
a connecting tube connected to and extending between the liquid driving device and the micro-pipe;
a vibrating equipment connected to the micro-pipe and adapted to directly vibrate the micro-pipe in an axial direction with respect to the longitudinal axis and transverse to the connecting tube, and the vibrating equipment is in coordination with the liquid driving device to dispense the first liquid from the micro-pipe and form a plurality of droplets of the first liquid in the second liquid.

7. The droplet generating system of claim 6, wherein the micro-pipe is disposed vertically.

8. The droplet generating system of claim 6, wherein the micro-pipe is disposed horizontally.

9. The droplet generating system of claim 6, wherein the container comprises a plurality of containers, the micro-pipe comprises a plurality of micro-pipes, and the outlet ends of the plurality of micro-pipes are respectively positioned in the plurality of containers.

10. The droplet generating system of claim 6, wherein the container is a well of a microplate.

11. A droplet generating apparatus comprising:
a liquid driving device configured to generate flow of a first liquid;
a micro-pipe extending along a vertical longitudinal axis, and including an outlet end;
a connecting tube in fluid communication with and extending between the liquid driving device and the micro-pipe, the connecting tube being horizontal and the first liquid flows from the liquid driving device through the connecting tube and is emitted out from the outlet end; and
a vibrating equipment operatively engaged to and adapted to vertically vibrate the micro-pipe along the longitudinal axis between a highest position and a lowest position, and thereby forming a plurality of droplets of the first liquid emitted from the outlet end.

12. The droplet generating system set forth in claim 11, further comprising:
a container positioned at least in-part below the micro-pipe and adapted to contain a second liquid including a liquid surface disposed at a position located between the highest and lowest positions for receipt of the droplets below the liquid surface.

13. The droplet generating system set forth in claim 7, wherein the vibrating equipment is adapted to vibrate the micro-pipe between a highest position and a lowest position, and the second liquid includes a liquid surface disposed at a position located between the highest position and the lowest position.

14. The droplet generating apparatus set forth in claim 1, wherein the vibrating equipment is adapted to vibrate the micro-pipe vertically between a highest position and a lowest position, and the second liquid includes a liquid surface disposed at a position located between the highest position and the lowest position.

* * * * *

SEQUENCE LISTING

<160> NUMBER OF SEQ ID NOS: 6

<210> SEQ ID NO 1
<211> LENGTH: 18
<212> TYPE: DNA
<213> ORGANISM: Artificial Sequence
<220> FEATURE:
<223> OTHER INFORMATION: Primer F3

<400> SEQUENCE: 1
gaatgcccgt tctgcgag                                              18

<210> SEQ ID NO 2
<211> LENGTH: 18
<212> TYPE: DNA
<213> ORGANISM: Artificial Sequence
<220> FEATURE:
<223> OTHER INFORMATION: Primer B3

<400> SEQUENCE: 2
ttcagttcct gtgcgtcg                                              18

<210> SEQ ID NO 3
<211> LENGTH: 41
<212> TYPE: DNA
<213> ORGANISM: Artificial Sequence
<220> FEATURE:
<223> OTHER INFORMATION: Primer FIP

<400> SEQUENCE: 3
cagcatccct ttcggcatac caggtggcaa gggtaatgag g                    41

<210> SEQ ID NO 4
<211> LENGTH: 40
<212> TYPE: DNA
<213> ORGANISM: Artificial Sequence
<220> FEATURE:
<223> OTHER INFORMATION: Primer BIP

<400> SEQUENCE: 4
ggaggttgaa gaactgcggc agtcgatggc gttcgtactc                      40

<210> SEQ ID NO 5
<211> LENGTH: 20
<212> TYPE: DNA
<213> ORGANISM: Artificial Sequence
<220> FEATURE:
<223> OTHER INFORMATION: Loop-F Primer

<400> SEQUENCE: 5
ggcggcagag tcataaagca                                            20

<210> SEQ ID NO 6
<211> LENGTH: 23
<212> TYPE: DNA
<213> ORGANISM: Artificial Sequence
<220> FEATURE:
<223> OTHER INFORMATION: Loop-B Primer

<400> SEQUENCE: 6
ggcagatctc cagccaggaa cta                                                                            23